United States Patent [19]

Atwal

[11] Patent Number: 5,470,975
[45] Date of Patent: Nov. 28, 1995

[54] DIHYDROPYRIMIDINE DERIVATIVES

[75] Inventor: Karnail Atwal, Newtown, Pa.

[73] Assignee: E.R. Squibb & Sons, Inc., Princeton, N.J.

[21] Appl. No.: 180,243

[22] Filed: Jan. 11, 1994

Related U.S. Application Data

[63] Continuation of Ser. No. 762,127, Sep. 23, 1991, abandoned, which is a continuation-in-part of Ser. No. 629,293, Dec. 14, 1990, abandoned, which is a continuation-in-part of Ser. No. 599,220, Oct. 16, 1990, abandoned.

[51] Int. Cl.$^6$ .................. C07D 239/20; C07D 239/22; C07D 239/72; C07D 239/78; C07D 239/80; C07D 239/84; C07D 239/88; C07D 239/93

[52] U.S. Cl. .................. 544/334; 544/295; 544/243; 544/244; 544/310; 544/311; 544/312; 544/313; 544/314; 544/319; 544/321; 544/330; 544/331; 544/332; 544/333; 544/335; 544/58.6; 544/60; 544/61; 544/82; 544/116; 544/117; 544/122; 544/123; 544/278; 544/279; 544/280; 544/283; 544/249; 544/284; 544/285; 544/286; 544/287; 544/289; 544/290; 544/292; 540/600; 540/601; 540/521

[58] Field of Search .................. 514/256, 269, 514/275, 257; 544/283, 243, 311, 315, 321, 332, 335, 295, 316, 317, 58.6, 82, 122, 279, 284, 287; 540/600

[56] References Cited

U.S. PATENT DOCUMENTS

| | | | |
|---|---|---|---|
| 4,880,804 | 11/1989 | Carini et al. | 514/234.5 |
| 5,100,897 | 3/1992 | Allen et al. | 544/319 |
| 5,268,375 | 12/1993 | Bernhart et al. | 514/269 |
| 5,330,987 | 7/1994 | Allen et al. | 514/258 |

FOREIGN PATENT DOCUMENTS

| | | |
|---|---|---|
| 0400835A1 | 12/1990 | European Pat. Off. . |
| 0400974A2 | 12/1990 | European Pat. Off. . |

OTHER PUBLICATIONS

D. J. Carini et al., "Nonpeptide Angiotensin II Receptor Antagonists: N-[(Benzyloxy)benzyl]imidazoles and Related Compounds as Potent Antihypertensives", *J. Med. Chem*, 1990, 33, pp. 1330–1336.

Atwal et al., Jour. of Med. Chem. vol. 35, pp. 4751–4763 (1992).

*Primary Examiner*—John M. Ford
*Attorney, Agent, or Firm*—Theodore R. Furman, Jr.; Ellen K. Park

[57] ABSTRACT

Novel A-II receptor antagonists have the formula

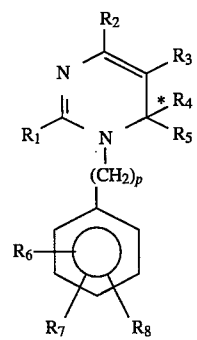

and its isomer

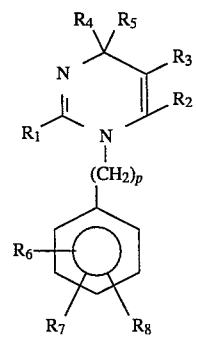

wherein $R_1$, $R_2$, $R_3$, $R_4$, $R_5$, $R_6$, $R_7$ and $R_8$ are as defined herein.

4 Claims, No Drawings

DIHYDROPYRIMIDINE DERIVATIVES

This is a continuation of U.S. Ser. No. 07/762,127, filed Sep. 23, 1991, now abandoned, which is a continuation-in-part of U.S. Ser. No. 629,293 filed Dec. 14, 1990, now abandoned, which is a continuation-in-part of U.S. Ser. No. 599,220 filed Oct. 16, 1990, now abandoned.

FIELD OF THE INVENTION

The present invention relates to novel dihydropyrimidine derivatives useful as antihypertensive agents.

SUMMARY OF THE INVENTION

In accordance with the present invention novel compounds, useful for example as antihypertensive agents, are disclosed. These compounds have the general formula

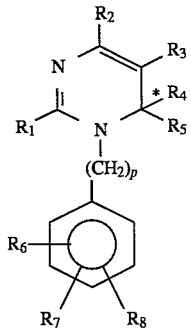

and its isomer

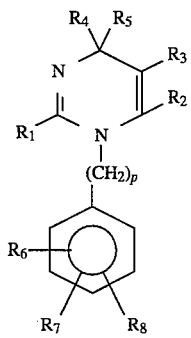

and pharmaceutically acceptable salts thereof wherein $R_1$ is alkyl of 1 to 10 carbon atoms, alkenyl or alkynyl of 3 to 10 carbon atoms or the same groups substituted with F or —$CO_2R_{22}$; cycloalkyl of 3 to 8 carbon atoms, cycloalkylalkyl of 4 to 10 carbon atoms, cycloalkylalkenyl or cycloalkylalkynyl of 5 to 10 carbon atoms; —$(CH_2)_sZ(CH_2)_mR'$ (wherein R' is H, $C_{1-6}$alkyl, $C_{3-6}$cycloalkyl, $C_{2-4}$alkenyl or $C_{2-4}$alkynyl) optionally substituted with F or —$CO_2R_{22}$; benzyl or benzyl substituted on the phenyl ring with 1 or 2 halogens, alkoxy of 1 to 4 carbon atoms, alkyl of 1 to 4 carbon atoms, haloalkyl or nitro; —$SR_4$, —$OR_4$ (where $R_4 \neq H$) or —$NR_4R_5$;

$R_2$ is hydrogen, halogen, $R_4'$, —CN, haloalkyl, —$OR_4$, —$SR_4$, —$COOR_4$, $COR_4$, ($R_4'O$)alkyl, ($R_4'S$)alkyl, (substituted amino)alkyl;

$R_3$ is $R_4$, —COOR, —$CONH_2$, —CO-substituted amino, —COR, —CN, —$NO_2$,

—$SO_2R$ (wherein R is $R_4$, aminoalkyl and (substituted amino)alkyl), ($R_4'O$)alkyl, ($R_4'S$)alkyl, (substituted amino)alkyl, ($R_4'OOC$)alkyl, ($R_4'CO$)alkyl, (amino-CO)alkyl, (substituted amino-CO)alkyl, (ROCO)alkyl (wherein R is $R_4$ excluding hydrogen);

or $R_2$ and $R_3$ taken together are

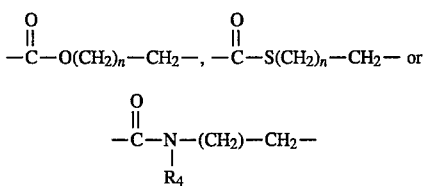

to form a 5- to 7-membered ring with the carbons to which they are attached;

$R_2$ and $R_3$ taken together with the carbon atoms to which they are attached form an aryl or heterocyclo;

$R_4$, $R_4'$ and $R_5$ are independently selected from hydrogen, alkyl, alkenyl, alkynyl, aryl, arylalkyl, cycloalkyl, (cycloalkyl)alkyl, heterocyclo, (heterocyclo)alkyl, haloalkyl;

or $R_4$ and $R_5$ taken together with the carbon atom to which they are attached form a 5- to 7-membered carbocyclic ring which may have another 5 to 7 membered ring fused thereto;

or $R_4$ and $R_5$ together with the carbon atoms to which they are attached form a carbonyl or a thiocarbonyl group;

$R_6$ is 4—$CO_2H$, 4—$CO_2R_9$,

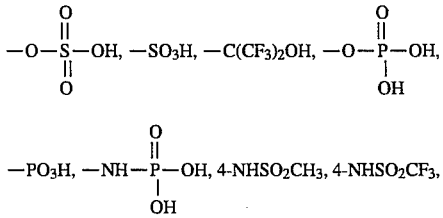

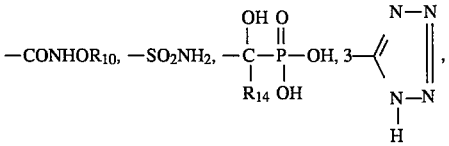

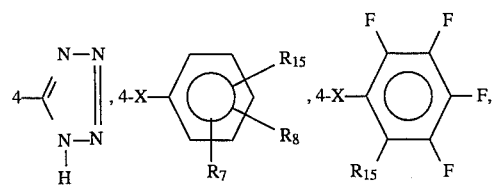

-continued

[structures: -NC(O)-CH=C(R15)-NC(O)- with 4X substituent on naphthalene; biphenyl with X and R15]

4-CONH-[tetrazole], 4-CONHNHSO$_2$CF$_3$,

4-CONH-CH(CO$_2$H)CH$_2$C$_6$H$_5$, 4-CO-N[pyrrolidine-CO$_2$H],

4-[furan/thiophene with HO$_2$C, R$_{19}$, R$_{19}$, Z], 4-[pyrazole-CF$_3$], 4-[triazole-NH-R$_{18}$],

[cyclohexane with R$_{15}$, 4-X], 4-N[phthalimide with R$_{15}$, R$_8$, R$_7$], $-\overset{O}{\underset{\|}{C}}-NHSO_2-(CH_2)_s-$[phenyl-R$_{20}$];

$R_7$ is H, halogen, —NO$_2$, —CN, alkyl of 1 to 4 carbons, acyloxy of 1 to 4 carbons, alkoxy of 1 to 4 carbons, —CO$_2$H, CO$_2$R$_9$, —NHSO$_2$CH$_3$, —NHSO$_2$CF$_3$, —CONHOR$_{10}$, —SO$_2$NH$_2$, aryl, furyl or

[tetrazole];

$R_8$ is H, halogen, alkyl of 1 to 4 carbons or alkoxy of 1 to 4 carbons;
$R_9$ is hydrogen or $-\overset{R_{10}}{\underset{|}{C}H}-O\overset{O}{\underset{\|}{C}}R_{11}$;

$R_{10}$ is hydrogen, methyl or benzyl;
$R_{11}$ is alkyl of 1 to 6 carbons, NR$_{12}$R$_{13}$;
$R_{12}$ and $R_{13}$ are independently hydrogen, benzyl, alkyl of 1 to 6 carbons or taken together are 3 to 6 methylene groups forming a 4- to 7-membered ring with the nitrogen atom to which they are attached;
$R_{14}$ is hydrogen, alkyl of 1 to 5 carbons or phenyl;
$R_{15}$ is —CO$_2$H, —CO$_2$R$_9$, —CH$_2$CO$_2$H, —CH$_2$CO$_2$R$_9$, $-O-\overset{O}{\underset{\underset{OH}{\|}}{S}}-OH$, $-O-\overset{O}{\underset{\underset{OH}{\|}}{P}}-OH$, $-SO_3H$, $-NH\overset{O}{\underset{\underset{OH}{\|}}{P}}-OH$,

—PO$_3$H, —C(CF$_3$)$_2$OH, —NHSO$_2$CH$_3$, —NHSO$_2$CF$_3$,

—NHCOCF$_3$, —CONHOR$_{10}$, —SO$_2$NH$_2$, $-\overset{OH}{\underset{\underset{R_{14}}{|}}{C}}-\overset{O}{\underset{\underset{OH}{\|}}{P}}-OH$,

[methyl-tetrazole-R$_{16}$], —CH$_2$-[tetrazole-H], —CONH-[tetrazole-H],

—CONHNHSO$_2$CF$_3$, [pyrazole-CF$_3$ with NH], [triazole-R$_{18}$ with NH];

$R_{16}$ is H, alkyl of 1 to 4 carbons, —CH$_2$CH=CH$_2$ or —CH$_2$C$_6$H$_4$R$_{17}$;
$R_{17}$ IS H, —NO$_2$, —NH$_2$, —OH or —OCH$_3$;
$R_{18}$ is —CN, —NO$_2$ or —CO$_2$R$_{19}$;
$R_{19}$ is H, alkyl of 1 to 6 carbons, cycloalkyl of 3 to 6 carbons, phenyl or benzyl;
$R_{20}$ and $R_{20}'$ are independently H, alkyl of 1 to 5 carbons or phenyl;
X is a carbon-carbon single bond, —CO—, —CH$_2$—, —O—, —S—, —NH—, $-\underset{R_{21}}{\underset{|}{N}}-$, $-\underset{R_{13}}{\underset{|}{CON}}-$, $-\underset{R_{13}}{\underset{|}{NCO}}-$, —CH$_2$O—, —SCH$_2$—, —CH$_2$—S—, —NHC(R$_{20}$)(R$_{20}'$), —NR$_{13}$SO$_2$—, —SO$_2$NR$_{13}$—, —C(R$_{20}$)(R$_{20}'$)NH, —CH=CH—, —CF=CF—, —CH=CF—, —CF=CH—, —CH$_2$CH$_2$—, —CF$_2$CF$_2$—, $-\underset{\underset{OR_{22}}{|}}{C}H-$, $-\underset{\underset{OCOR_{19}}{|}}{C}H-$, $-\underset{\underset{NR_{23}}{\|}}{C}-$ or $-\underset{\underset{R_{24}O\;\;OR_{25}}{\diagup\;\;\diagdown}}{C}-$ ;

$R_{21}$ is H, alkyl of 1 to 6 carbons, benzyl or alkyl;
$R_{22}$ is H, alkyl or perfluoroalkyl of 1 to 8 carbons, cycloalkyl of 3 to 6 carbons, phenyl or benzyl;
$R_{23}$ is —N(R$_{20}$)(R$_{20}'$), —NHCONH$_2$, —NHCSNH$_2$, —NHSO$_2$-[phenyl]-CH$_3$ or —NHSO$_2$-[phenyl];

$R_{24}$ and $R_{25}$ are independently alkyl of 1 to 4 carbons or taken together are —(CH$_2$)$_q$;
Z is O, NR$_{19}$ or S;

m is 1 to 5;

n is 0 to 2;

p is 0 to 2;

q is 2 or 3; and s is 0 to 5.

DETAILED DESCRIPTION OF THE INVENTION

In its broadest aspects the present invention relates to the compounds of formula I and I' and to pharmaceutical compositions and methods employing such compounds.

The term "alkyl", as used throughout the specification either by itself or as part of a larger group, refers to groups having 1 to 10 carbon atoms. Alkyl groups having 1 to 4 carbon atoms are preferred.

The term "cycloalkyl", as used throughout the specification either by itself or as part of a larger group, refers to groups having 3 to 7 carbon atoms.

The term "alkoxy", as used throughout the specification either by itself or as part of a larger group, refers to groups having 1 to 8 carbon atoms. Alkoxy groups having 1 to 3 carbon atoms are preferred.

The term "halogen", as used by itself or as part of a larger group refers to fluorine, chlorine, bromine and iodine with fluorine and chlorine being preferred.

The term "alkenyl" and "alkynyl" refer to both straight and branched chain groups. Those groups having 2 to 10 carbon atoms are preferred.

The term "haloalkyl" refers to such alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term "aryl" refers to phenyl, 1-naphthyl, 2-naphthyl, monosubstituted phenyl, 1-naphthyl, or 2-naphthyl wherein said substituent is alkyl of 1 to 4 carbons, alkylthio of 1 to 4 carbons, alkoxy of 1 to 4 carbons, halo, nitro, cyano, hydroxy, amino, —NH-alkyl wherein alkyl is of 1 to 4 carbons, —N(alkyl)$_2$ wherein alkyl is of 1 to 4 carbons, CF$_3$, OCHF$_2$,

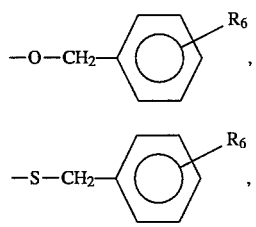

—OCH$_2$-cycloalkyl, or —S—CH$_2$-cycloalkyl, and disubstituted phenyl, 1-naphthyl, or 2-naphthyl wherein said substituents are selected from methyl, methoxy, methylthio, halo, CF$_3$, nitro, amino, and OCHF$_2$.

The term "heterocyclo" refers to fully saturated or unsaturated rings of 5 or 6 atoms containing one to four N atoms, or one O atom, or one S atom, or one O atom and one or two N atoms, or one S atom and one or two N atoms. The heterocyclo ring is attached by way of an available carbon atom. Preferred monocyclic heterocyclo groups include 2- and 3-thienyl, 2- and 3-furyl, 2-, 3- and 4-pyridyl, and imidazolyl. The 2-, 3- and 4-pyridyl may also have a substituent selected from alkyl of 1 to 4 carbons, alkoxy of 1 to 4 carbons and alkylthio of 1 to 4 carbons on an available carbon. The term heterocyclo also includes bicyclic rings wherein the five or six membered ring containing O, S and N atoms as defined above is fused to a benzene ring and the bicyclic ring is attached by way of an available carbon atom in the benzene ring. Preferred bicyclic heterocyclo groups include 4, 5, 6 or 7-indolyl, 4, 5, 6 or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofurazanyl.

The term "substituted amino" refers to a group of the formula —NZ$_1$Z$_2$ wherein Z$_1$ is hydrogen, alkyl, or aryl—(CH$_2$)$_m$— and Z$_2$ is alkyl or aryl—(CH$_2$)$_m$— (where m is 0 to 2) or Z$_1$ and Z$_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, or 1-pyrrolidinyl, 1-piperidinyl, or 1-azepinyl substituted with alkyl, alkoxy, alkylthio, halo, trifluoromethyl or hydroxy.

The compounds of formula I can be prepared by coupling a compound of the formula

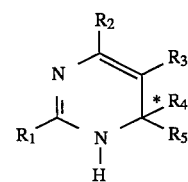

with a compound of the formula

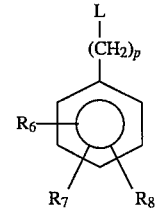

(wherein L is a leaving group, e.g., halogen,

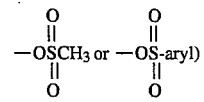

in the presence of a base, such as potassium carbonate, and in an organic solvent, such as dimethylformamide. The alkylation of compound II with compound III to give compound I is sometimes accompanied by the isomeric product I' which can be separated from product I by conventional chromatographic or crystallization techniques. When R$_4$ and R$_5$ are both alkyl groups (e.g., methyl) or taken together they form a spirocarboxylic ring, I' becomes the exclusive product of alkylation. If any of R$_6$–R$_8$ contain functional groups (e.g., carboxy, hydroxy, amino groups) that can interfere with the alkylation of II, then such groups should be protected during the reaction. Suitable protecting groups include t-butoxycarbonyl, benzyl, triphenyl methyl, etc.

Compounds of formula II wherein R$_2$ is halogen, e.g., chloro, and R$_3$ is —COOR can be prepared by first reacting an amidine of the formula

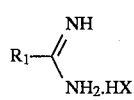   IV (wherein X is halogen)
with an olefin of the formula

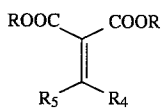   V in an organic solvent, such as diemthylformamide, and in the presence of a base, such as potassium carbonate or potassium ter-butoxide, to provide a pyrimidine of the formula

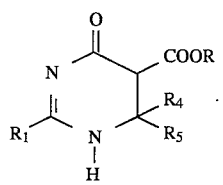   VI

The pyrimidine of formula VI can thereafter be heated in the presence of a chlorinating agent, e.g., phosphorus oxychloride to provide the intermediates of formula II where $R_2$ is chloro and $R_3$ is —COOR. Compounds of formula II where $R_2$ is a halogen other than chloro can be made in a similar fashion.

To provide the intermediates of formula II wherein $R_2$ is other than halogen, first the amidine of formula IV can be reacted with an olefin of the formula

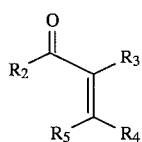   VII in the presence of, for example, sodium bicarbonate, and in a solvent, e.g., dimethylformamide to provide an intermediate of the formula

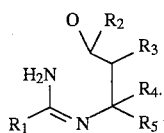   VIII

Intermediate VIII can thereafter be cyclized, e.g., by heating in the presence of an acid, such as p-toluenesulfonic acid, and in an organic solvent, such as benzene or dimethylformamide, to provide compounds of formula II where $R_2$ is other than halogen. Compounds of formula II, wherein $R_4$ and $R_5$ together with the carbon atom to which they are attached form a carbonyl group, can be prepared by reacting compound of the formula

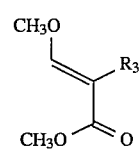   IX with an amidine of formula IV in the presence of sodium bicarbonate or sodium acetate. These compounds (i.e., $R_4$ and $R_5$ together with the carbon atom to which they are attached form a carbonyl group) can also be prepared by oxidation of a compound of formula VI with oxidizing agents, such as manganese oxide, dichlorodicyanoquinone, etc.

Alternatively, compounds of formula II wherein $R_4$ and $R_5$ are a carbonyl group can be prepared by reacting a compound of the formula

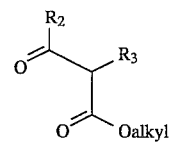   X with an amidine of formula IV in the presence of sodium bicarbonate or sodium acetate in a polar solvent such as ethanol, dimethylformamide. Other dihydropyrimidines of formula II can be prepared by methods described in the literature, e.g., K. Atwal et al., *J. Org. Chem.*, Vol. 54, p. 5898 (1989) and references therein.

Compounds of formula III can be prepared as described in European Patent Application 0 253 310 to DuPont.

The compounds of formula I and I' can have an asymmetric center within the pyrimidine ring as represented by the *. Also, any of the R groups can have an asymmetric center. Thus, the compounds of formula I can exist in diastereomeric forms or in mixtures thereof. The above-described processes can utilize racemates, enantiomers or diastereomers as starting materials. When diastereomeric products are prepared, they can be separated by conventional chromatographic or fractional crystallization methods.

If any of the R groups in the above are aryl, or terminate in aryl wherein aryl is phenyl, 1-naphthyl, or 2-naphthyl substituted with one or more hydroxy or amino groups or heterocyclo, wherein the heterocyclo ring contains an NH such as imidazolyl, or an alkyl substituted for example with hydroxyl, amino or mercapto, then the hydroxyl, amino, or mercaptan function should be protected during the reaction. Suitable protecting groups include benzyloxycarbonyl, t-butoxycarbonyl, benzyl, benzhydryl, etc. The protecting group is removed by hydrogenation, treatment with acid, or by other known means following completion of the reaction.

Preferred compounds of the present invention are those wherein
$R_1$ is alkyl of 3 to 5 carbons;
$R_2$ is H, alkyl, haloalkyl, chloro or aryl;
$R_3$ is —COOR;
$R_4$ is hydrogen or alkyl;
$R_5$ is alkyl or aryl;
$R_4$ and $R_5$ together with the carbon atom to which they are attached form a carbonyl group;
$R_6$ is —COOH or tetrazole;
$R_7$ is alkyl or hydrogen; and,
$R_8$ is hydrogen.

Most preferred compounds of the present invention are those wherein
$R_1$ is n-butyl;

$R_2$ is H, —$CF_3$, chloro, phenyl or 4-chlorophenyl;
$R_3$ is —$COOC_2H_5$;
$R_4$ is hydrogen or methyl;
$R_5$ is methyl or aryl;
$R_4$ and $R_5$ together with the carbon atom to which they are attached form a carbonyl group;
$R_6$ is 2—COOH or 2-tetrazole;
$R_7$ is hydrogen; and,
$R_8$ is hydrogen.

The present compounds of formula I and I' inhibit the action of the hormone angiotensin II (A-II) and are therefore useful, for example, as antihypertensive agents.

The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention inhibit the action of A-II at its receptors on target cells and thus prevent the increase in blood pressure produced by this hormone-receptor interaction. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg per kilogram of body weight per day, preferably about 1 to 15 mg per kilogram of body weight per day is appropriate to reduce blood pressure. The substance is preferably administered orally, but intranasal, transdermal and parenteral routes such as the subcutaneous, intramuscular, intravenous or intraperitoneal routes can also be employed. The compounds of this invention are also useful in the treatment/prevention of congestive heart failure, cardiac hypertrophy, loss of cognitive function, renal failure and are useful for kidney transplant.

The compounds of this invention can also be formulated in combination with a diuretic for the treatment of hypertension or congestive heart failure. A combination product comprising a compound of this invention and a diuretic can be administered in an effective amount which comprises a total daily dosage of about 30 to 600 mg, preferably about 30 to 330 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorthiazide, hydrochlorthiazide, flumethiazide, hydroflumethiazide, bendroflumethiazide, methylchlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I and I' can be formulated for use in the reduction of blood pressure in compositions such as tablets, capsules or elixirs for oral administration, in sterile solutions or suspensions for parenteral or intranasal administration, or in transdermal patches. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The present invention can be further illustrated by the following example.

EXAMPLE 1

2-Butyl-1-[[2'-carboxy[1,1'-biphenyl]-4-yl]-methyl]-4-chloro-1,6-dihydro-6-methyl-1-pyrimidine-5-carboxylic acid, ethyl ester A. Pentanimidamide, Monohydrochloride Ammonia gas was slowly bubbled through absolute ethanol (125 mL) at 0° C. (ice bath) for 20 minutes. To the resulting solution was added pentanimidic acid, ethyl ester, monohydrochloride (25 g, 151 mmol) in one portion. The reaction mixture was stirred at 0° C. for 30 minutes to give a clear solution. It was allowed to stand at 0° C. for 3 more hours and the solvent was evaporated under reduced pressure to yield the title A compound as a light yellow semisolid (22 g) which was used for the next reaction without purification.

B. (trans)-2-Butyl-1,4,5,6-tetrahydro-6-methyl-4-oxo-5-pyrimidinecarboxylic Acid, Ethyl Ester To the solution of diethyl ethylidenemalonate (4.62 mL, 25.3 mmol) in dimethylformamide (12 mL) was added the title A compound (3.46 g, 25.3 mmol) and sodium bicarbonate (6.3 g, 275.0 mmol) at room temperature under argon. The reaction mixture was allowed to stir at room temperature for 14 hours and diluted with ethyl acetate. The insoluble material was filtered off and the filtrate was washed with saturated sodium bicarbonate, water and brine. After drying over anhydrous magnesium sulfate, the solvent was evaported and the residue was triturated with isopropyl ether to yield an offwhite solid (2.54 g). The mother liquour was purified by flash chromatography on silica gel (15% acetone in dichloromethane) to give a light yellow oil (1.66 g) for a total of 4.2 g of the title B compound. $^1$H NMR ($CDCl_3$) δ 9.8 (br s, 1H), 4.24 (q, J=7.0 Hz, 2H), 4.12 (m, 1H), 3.2 (d, J=10.0 Hz, 1H), 2.3 (t, J=7.6 Hz, 2H), 1.6 (qn, J=7.6 Hz, 2H), 1.37 (m, 2H), 1.4–1.2 (m, 5H), 0.92 (t, J=7.6 Hz, 3H); $^{13}$C NMR ($CDCl_3$) 168.4, 168.1, 153.4, 61.7, 52.8, 52.75, 35.0, 28.2, 22.1, 20.4, 14.0, 13.6 ppm.

C. 6-Butyl-4-chloro-1,2-dihydro-2-methyl-3-pyrimidinecarboxylic Acid, Ethyl Ester The reaction mixture containing the title B ester (1.66 g, 6.9 mmol) and phosphorus oxychloride (28 mL) was heated at reflux temperature (oil bath temperature 120° C.) for 6 hours under argon. The excess phosphorus oxychloride was evaporated under reduced pressure and the residue was coevaporated with toluene twice to give the title C compound as an oil (1.8 g crude) which was used for the next reaction without further purification. $^1$H NMR ($CDCl_3$) δ 4.70 (q, J=6.5 Hz, 1H), 4.2 (m, 2H), 2.4 (t, J=7.6 Hz, 2H), 1.7 (qn, J=7.6 Hz, 2H), 1.4–1.2 (m, 5H), 0.92 (t, J=7.6 Hz, 3H); $^{13}$C NMR ($CDCl_3$) 164.1, 144.6, 103.6, 60.6, 47.9, 34.2, 29.3, 23.4, 22.2, 14.1, 13.6 ppm.

D. 6-Butyl-4-chloro-1-[2'-[(1,1-dimethylethoxy)-carbonyl][1,1'-biphenyl]-4-yl]-1,2-dihydro-2-methyl-3-pyrimidinecarboxylic Acid, Ethyl Ester The solution of the title C compound (1.9 g, crude) in dimethylformamide (14 mL) was treated with finely ground potassium carbonate (3.87 g, 27.4 mmol) and 4'-(bromomethyl)[1,1'-biphenyl]-2-carboxylic acid, 1,1-dimethylethyl ester (2.51 g, 8.3 mmol, prepared according to EP 253,310 to DuPont). The reaction mixture was allowed to stir at room temperature overnight. Some unreacted starting material was still present. More potassium carbonate (3.8 g) and bromide (1.1 g) were added and the reaction mixture was stirred for 15 more hours. It was diluted with ethyl acetate and filtered. The filtrate was washed with water, brine and dried over anhydrous magnesium sulfate. The solvent was evaporated to yield a yellow oil which was purified by flash chromatography on silica gel (15% ethyl acetate in hexanes) to provide the title D compound as a yellow foam (2.58 g, 71%). $^1$H NMR (CDCl$_3$) δ 7.88 (d, J=7.6 Hz, 1H), 7.6–7.3 (m, 7H), 4.92 (d, J=16.4 Hz, 1H), 4.6 (m, 2H), 4.25 (m, 2H), 2.5 (m, 2H), 1.65 (m, 2H), 1.5–1.3 (m, 17H), 1.0 (t, J=7.0 Hz, 3H); $^{13}$C NMR (CDCl$_3$) 167.7, 164.2, 163.9, 148.2, 141.8, 141.1, 134.1, 132.6, 130.7, 130.4, 129.7, 129.3, 129.2, 128.6, 127.3, 125.9, 101.9, 81.2, 77.2, 60.2, 54.1, 52.3, 34.0, 29.1, 27.6, 22.5, 18.4, 14.2, 13.7 ppm.

E. 2-Butyl-1-[[2'-carboxy[1,1'-biphenyl]-4-yl]-methyl]-4-chloro-1,6-dihydro-6-methyl-1-pyrimidine-5-carboxylic Acid, Ethyl Ester To the solution of the title D compound (2.58 g, 4.92 mmol) in dichloromethane (20 mL) was added trifluoroacetic acid (8.0 mL) and the reaction mixture was stirred at room temperature for 3 hours. The solvent was evaporated and the residue was purified by flash chromatography on silica gel (3% methanol in dichloromethane) to give an offwhite solid (1.14 g). This material was recrystallized from ether (containing few drops of methanol) to provide the title compound (456 mg), m.p. 93°–95° C. $^1$H NMR (CDCl$_3$) δ 7.94 (d, J=6.5 Hz, 1H), 7.5 (t, J=7.7 Hz, 1H), 7.5–7.2 (m, 6H), 4.80 (d, J=15.8 Hz, 1H), 4.5 (m, 2H), 4.25 (m, 2H), 2.4 (m, 2H), 1.6 (m, 2H), 1.36 (m, 2H), 1.24 (d, J=7.0 Hz, 3H), 1.2 (t, J=6.5 Hz, 3H), 0.9 (t, J=7.0 Hz, 3H); $^{13}$C NMR (CDCl$_3$)171.5, 164.5, 164.3, 147.5, 142.1, 141.5, 134.0, 131.6, 130.8, 130.5, 130.3, 129.3, 127.4, 126.2, 102.1, 77.2, 60.4, 54.0, 52.5, 33.6, 29.2, 22.5, 18.4, 14.2, 13.6 ppm.

Analysis calc'd for $C_{26}H_{29}ClN_2O_4 \cdot 0.27\ H_2O$: C, 65.90; H, 6.28; N, 5.91; Cl, 7.48; Found: C, 66.30; H, 6.81; N, 5.51; Cl, 7.50.

EXAMPLE 2

2-Butyl-1-[[2'-carboxy[1,1'-biphenyl]-4-yl]-methyl]-1,6-dihydro-6-oxo-pyrimidine-5-carboxylic Acid Methyl Ester A.
2-Butyl-1,6-dihydro-6-oxo-pyrimidine-5-Carboxylic Acid Methyl Ester The reaction mixture containing pentanimidine, monohydrochloride (1.56 g, 11.5 mmol), dimethyl methoxymethylenemalonate (2.0 g, 11.5 mmol, prepared according to L. Combie, D. E. Games and A. W. G. James, *J.C.S. Perkin I*, 1979, 464) and sodium bicarbonate (2.9 g, 3.45 mmol) in dimethylformamide (6.5 mL) was stirred at room temperature under argon for 5 hours. It was heated at 60° C. overnight, cooled to ambient temperature and diluted with ethyl acetate. The solid was filtered off and the filtrate was washed with water, brine and dried over anhydrous magnesium sulfate. The solvent was evaporated and the oily residue (1.54 g) was purified by flash chromatography (5% acetone in dichloromethane). The desired product was crystallized from dichloromethane-isopropyl ether to give the title A compound as a colorless solid (195 mg), m.p. 153°–155° C. $^1$H NMR (CDCl$_3$) δ 8.75 (s, 1H), 3.9 (s, 3H), 2.8 (t, J=7.6 Hz, 2H), 1.8 (qn, J=8 Hz, 2H), 1.45 (qn, J=7.0 Hz, 2H), 0.95 (t, J=7.0 Hz, 3H); $^{13}$C NMR (CDCl$_3$) 167.8, 164.1, 161.7, 161.1, 114.4, 52.1, 35.2, 29.2, 22.1, 13.5.

B. 2-Butyl-1-[2'-[(1,1-dimethylethoxy)carbonyl]-[1,1'-biphenyl]-4-yl]-1,6-dihydro-6-oxo-pyrimidine-5-carboxylic Acid Methyl Ester To a solution of the title A compound (180 mg, 0.86 mmol) in dimethylformamide (2.0 mL) under argon was added finely ground potassium carbonate (356 mg, 2.58 mmol) and 4'-bromomethyl)[1,1'-biphenyl]-2-carboxylic acid, 1,1-dimethylethyl ester (311 mg, 1.03 mmol, prepared according to EP 253,310 to DuPont). The reaction mixture was allowed to stir at room temperature overnight and diluted with ethyl acetate. The solid was filtered off and the filtrate was washed with water, brine and dried over anhydrous magnesium sulfate. The solvent was evaporated and the residue was purified by flash chromatography (20–40% ethyl acetate in hexanes) to give the title B compound (196 mg). $^1$H (CDCl$_3$) δ 8.7 (s, 1H), 7.8 (d, J=7.0 Hz, 1H), 7.5 (t, J=7.0 Hz, 1H), 7.4 (t, J=7.0 Hz, 1H), 7.2 (m, 5H), 5.4 (s, 2H), 3.9 (s, 3H), 2.78 (t, J=7.6 Hz, 2H), 1.72 (qn, J=7.6 Hz, 2H), 1.38 (qn, J=7.6 Hz, 2H), 1.25 (s, 9H), 0.92 (t, J=7.6 Hz, 3H); $^{13}$C NMR (CDCl$_3$) 167.7, 167.4, 159.0, 158.1, 141.8, 141.2, 133.7, 130.7, 130.4, 129.7, 129.2, 127.3, 126.6, 114.4, 81.3, 52.4, 46.30, 35.4, 28.7, 27.6, 27.6, 22.3, 13.7 ppm.

C.
2-Butyl-1-[[2'-carboxy[1,1'-biphenyl]-4-yl]-methyl]-1,6-dihydro-6-oxo-pyrimidine-5-carboxylic Acid Methyl Ester To the solution of the title B compound (180 mg, 0.38 mmol) in dichloromethane (5 mL) was added trifluoroacetic acid (1 mL) and the reaction mixture was stirred at room temperatur for 2 hours. The solvent was evaporated and the residue was purified by flash chromatography on silica gel (3–10% methanol in dichloromethane) to give a colorless oil which was crystallized from ethanol-ether to yield the title compound as a colorless solid (59 mg), m.p. 166°–168° C. $^1$H NMR (CDCl$_3$) δ 9.66 (br s, 1H), 8.7 (s, 1H), 7.9 (d, J=7.6 Hz, 1H), 7.5 (t, J=7.6 Hz, 1H), 7.4 (t, J=7.7 Hz, 1H), 7.3–7.1 (m, 5H), 5.38 (s, 2H), 3.9 (s, 3H), 2.77 (t, J=7.0 Hz, 2H), 1.6 (qn, J=7.0 Hz, 2H), 1.36 (qn, J=7.6 Hz, 2H), 0.84 (t, J=7.6 Hz, 3H); $^{13}$C NMR (CDCl$_3$) 172.0, 167.9, 164.4, 159.0, 157.7, 142.0, 141.1, 133.6, 131.6, 130.9, 130.4, 130.1, 129.1, 127.3, 126.5, 114.2, 76.5, 52.3, 46.7, 35.1, 28.8, 22.2, 20.8, 13.5 ppm.

Analysis calc'd for $C_{24}H_{24}N_2O_5 \cdot 0.25\ H_2O$: C, 67.84; H, 5.81; N, 6.59; Found: C, 67.61; H, 5.83; N, 6.46.

EXAMPLE 3

2-Butyl-1-[[2'-carboxy[1,1'-biphenyl]-4-yl]-methyl]-1,6-dihydro-5-methyl-6-oxo-pyrimidine-4-carboxylic Acid Ethyl Ester Monosodium Salt A.
2-Butyl-1,6-dihydro-5-methyl-6-oxo-pyrimidine-4-carboxylic Acid Ethyl Ester The reaction mixture containing pentanimidine, monohydrochloride (2.95 g, 21.6 mmol), diethyl oxalpropionate (4.1 mL, 21.6 mmol) and sodium bicarbonate (2.9 g, 3.45 mmol) in dimethylformamide (6.5 mL) was stirred at room temperature under argon for 5 hours. It was heated at 90° C. overnight, cooled to ambient temperature and diluted with ethyl acetate. The solid was filtered off and the filtrate was washed with water, brine and dried over anhydrous magnesium sulfate. The solvent was evaporated and the brown oily residue was purified by flash chromatography (15% ethyl acetate in dichloromethane) to yield the title A compound as a light yellow solid (1.6 g). $^1$H NMR (CDCl$_3$) δ 4.4 (m, 2H), 2.7 (t, J=7.0 Hz, 2H), 2.2 (s, 3H), 1.78 (m, 2H), 1.4 (m, 5H), 0.95 (t, J=7.0 Hz, 3H); $^{13}$C NMR (CDCl$_3$) 165.9, 165.7, 160.1, 151.6, 122.00, 62.0, 35.0, 29.6, 22.2, 14.1, 13.6, 11.1 ppm.

B. 2-Butyl-1-[2'-[(1,1-dimethylethoxy)-carbonyl][1,1'-biphenyl]-4-y]-1,6-dihydro-5-methyl-6-oxo-pyrimidine-5-carboxylic Acid Methyl Ester To a solution of the title A compound (1.6 g, 7.13 mmol) in dimethylformamide (10 mL) under argon was added finely ground potassium carbonate (2.95 g, 21.4 mmol) and 4'-(bromomethyl)[1,1'-biphenyl]-2-carboxylic acid, 1,1-dimethylethyl ester (2.3 g, 7.13 mmol, prepared according to EP 253,310 to DuPont). The reaction mixture was allowed to stir at room temperature overnight and diluted with ethyl acetate. The solid was filtered off and the filtrate was washed with water, brine and dried over anhydrous magnesium sulfate. The solvent was evaporated and the residue was purified by flash chromatography (15–25% ethyl acetate in hexanes) to give the title B compound (1.56 g) as a colorless oil. $^1$H (CDCl$_3$) δ 7.78 (d, J=7.6 Hz, 1H), 7.45 (t, J=7.0 Hz, 1H), 7.40 (t, J=7.0 Hz, 1H), 7.27 (m, 3H), 7.18 (d, J=7.6 Hz, 2H), 5.36 (s, 2H), 4.42 (q, J=7.0 Hz, 2H), 2.73 (t, J=7.0 Hz, 2H), 2.26 (s, 3H), 1.72 (qn, J=7.6 Hz, 2H), 1.41 (t, J=7.0 Hz, 2H), 1.25 (s, 9H), 0.92 (t, J=7.0 Hz, 3H); $^{13}$C NMR (CDCl$_3$) 167.7, 165.8, 163.6, 159.9, 148.8, 141.5, 141.2, 134.0, 132.7, 130.6, 130.4, 129.6, 129.1, 127.2, 126.2, 121.9, 81.2, 77.2, 61.9, 46.8, 34.9, 29.0, 27.5, 22.3, 14.1, 13.7, 12.2 ppm.

C. 2-Butyl-1-[[2'-carboxy[1,1'-biphenyl]-4-yl]-methyl]-1,6-dihydro-5-methyl-6-oxo-pyrimidine-4-carboxylic Acid Ethyl Ester Monosodium Salt To the solution of the title B compound (1.56 g, 3.09 mmol) in dichloromethane (15 mL) was added trifluoroacetic acid (3 mL) and the reaction mixture was stirred at room temperature for 2 hours. The solvent was evaporated and the residue was purified by flash chromatography on silica gel (35% acetone in hexanes) to give a colorless foam (1.39 g). It was dissolved in tetrahydrofuran (10 mL) and treated with 1N sodium hydroxide. The solvent was evaporated and the residue was stirred with 10% aqueous acetone to yield the title compound as a colorless solid (220 mg), m.p. 139°–141° C. (softens at 100° C.). $^1$H NMR (CDCl$_3$, free acid) δ 9.7 (br s, 1H), 7.9 (d, J=7.6 Hz, 1H), 7.5 (t, J=7.6 Hz, 1H), 7.42 (t, J=7.7 Hz, 1H), 7.28 (t, J=8.0 Hz, 3H), 7.15 (d, J=8.2 Hz, 2H), 5.36 (s, 2H), 4.43 (q, J=7.0 Hz, 2H), 2.74 (t, J=7.0 Hz, 2H), 2.26 (s, 3H), 1.64 (m, 2H), 1.34 (t, J=7.0 Hz, 3H), 0.85 (t, J=7.6 Hz, 3H); $^{13}$C NMR (CDCl$_3$) 172.2, 165.3, 163.7, 160.6, 148.2, 142.5, 140.9, 134.0, 131.9, 131.1, 130.6, 129.4, 129.1, 127.3, 126.3, 122.3, 77.2, 62.0, 47.1, 34.3, 29.3, 22.3, 14.0, 13.6, 12.2 ppm.

Analysis calc'd for C$_{26}$H$_{27}$N$_2$O$_5$Na.1.0 H$_2$O: C, 63.93; H, 5.98; N, 5.73; Na, 4.71; Found: C, 64.22; H, 6.02; N, 5.61; Na, 4.54.

EXAMPLE 4

2-Butyl-4-chloro-1,6-dihydro-6-methyl-1-[[2'-(1H-tetrazole-5-yl)[1,1'-biphenyl]-4-yl]methyl]-pyrimidine-5-carboxylic Acid, Ethyl Ester, Monopotassium Salt

A. 2-Butyl-4-chloro-1,6-dihydro-6-methyl-1-[[2'-(1-(triphenylmethyl)tetrazole-5-yl)-[1,1'-biphenyl]-4-yl]methyl]pyrimidine-5-carboxylic Acid, Ethyl Ester The solution of compound C from Example 1 (780 mg, 3.04 mmol) in dimethylformamide (7 mL) was treated with finely ground potassium carbonate (1.66 g, 12.0 mmol) and N-triphenylmethyl-5-[2-(4'-bromomethyl-biphenylyl)tetrazole (2.54 g, 4.55 mmol, prepared according to U.S. Pat. No. 4,874,876). The reaction mixture was allowed to stir at room temperature overnight. More bromide (500 mg) was added and the reaction mixture was heated at 65° C. for 8 hours. It was diluted with ethyl acetate and filtered. The filtrate was washed with water whereby a colorless precipitate came out of the solution. The two phase solution was filtered through a celite pad, the organic layer was separated and washed with water, brine and dried over anhydrous magnesium sulfate. The solvent was evaporated to yield a yellow foam which was purified by flash chromatography on silica gel (15% acetone in hexanes) to provide the title A compound (1.2 g) as a light yellow foam. $^1$H NMR (CDCl$_3$) δ 8.05 (dd, J=7.0 and 1.2 Hz, 1H), 7.7–6.9 (m, 22H), 4.73, 4.42 (ABq, J=16.4 Hz, 2H), 4.53 (q, J=6.0 Hz, 1H), 4.24 (m, 2H), 2.4 (m, 2H), 1.70 (m, 2H), 1.4 (m, 2H), 1.3 (m, 6H), 1.0 (t, J=7.0 Hz, 3H); $^{13}$C NMR (CDCl$_3$) 164.0, 163.2, 141.3, 141.2, 133.8, 130.6, 130.2, 130.0, 128.3, 127.7, 127.6, 126.2, 125.7, 102.0, 82.0, 60.2, 54.1, 52.2, 34.0, 29.0, 22.5, 18.4, 14.2, 13.7 ppm.

B. 2-Butyl-4-chloro-1,6-dihydro-6-methyl-1-[[2'-(1H-tetrazole-5-yl)[1,1'-biphenyl]-4-yl]methyl]pyrimidine-5-carboxylic acid, Ethyl Ester, Monopotassium Salt To the solution of the title A compound (1.02 g, 1.38 mmol) in tetrahydrofuran (10 mL) and water (2 mL) was added trifluoroacetic acid (3.0 mL) and the reaction mixture was stirred at room temperature overnight. The reaction was diluted with toluene (100 mL) and evaporated. The residue was purified by flash chromatography on silica gel (7% methanol in dichloromethane) to give a light yellow foam (685 mg). This material was dissolved in tetrahydrofuran (10 mL) and treated with 1N potassium hydroxide (1.5 mL). Most of the solvent was evaporated and the residue was passed through an HP-20 column eluting with 70–90% methanol in water. The fractions containing the desired material were pooled together and evaporated. The residue in water (7.0 mL) (traces of methanol added until clear solution was obtained) was lyophilized to yield the title compound as a light yellow solid (402 mg), shrinks at 130°–135° C. $^1$H NMR (CD$_3$OD) δ 7.4 (m, 4H), 7.25 (s, 4H), 4.7, 4.46 (ABq, J=16 Hz, 2H), 4.4 (q, J=6.0 Hz, 1H), 4.03 (m, 2H), 2.25 (m, 2H), 1.4 (m, 2H), 1.25 (m, 2H), 1.1 (t, 6.0 Hz, 3H), 1.04 (d, J=6.0 Hz, 3H), 0.8 (t, J=7.0 Hz, 3H); $^{13}$C NMR (CD$_3$OD) 166.6, 165.5, 162.2, 148.6, 142.6, 142.3, 135.5, 131.8, 131.3, 130.9, 130.3, 128.3, 127.4, 103.1, 61.5, 55.1, 53.4, 34.4, 30.3, 23.4, 18.4, 14.6, 14.0 ppm.

Analysis calc'd for C$_{26}$H$_{29}$ClN$_6$O$_2$K.0.5 H$_2$O: C, 57.83; H, 5.41; N, 15.56; Cl, 6.57; Found: C, 57.90; H, 5.77; N, 15.49; Cl, 6.66.

EXAMPLE 5

2-Butyl-1-[[2'-carboxy[1,1'-biphenyl]-4-yl]methyl]-1,6-dihydro-4,6-dimethyl-5-pyrimidinecarboxylic Acid, Ethyl Ester, Trifluoroacetate

A. Ethyl-2-(ethylidine) Acetoacetate

To a mixture of ethyl acetoacetate (13.0 g, 100 mmol) and acetaldehyde (94.8 g, 109 mmol) at −5° C. was added piperdine (0.3 g, 3.5 mmol) and the mixture was kept at this temperature for 48 hours. The reaction mixture was then neutralized with 10% sulfuric acid and diluted with ethyl ether. Organic layer was separated and washed with water (100 ml), dried over anhydrous magnesium sulfate and concentrated in vacuo to give 9.6 g of the title A compound as an oil. $^1$H NMR (CDCl$_3$) δ 7.0 (m, 1H), 4.36 (m, 2H), 2.40 (s, 3H), 2.04 (d, J=7.7 Hz, 3H), 1.38 (m, 3H).

B. 2-Butyl-1,6-dihydro-4,6-dimethyl-5-pyrimidinecarboxylic Acid, Ethyl Ester To a solution of the title A compound of Example 1 (2.89 g, 21.1 mmol) in dimethylformamide (40 mL) was added potassium t-butoxide (2.2 g, 19.2 mmol) under argon and the reaction mixture was stirred for ~15 minutes. A solution of the title A compound (3.0 g, 19.2 mmol) in dimethylformamide (10 ml) was added and the reaction mixture was stirred for ~15 minutes at 0° C. and then p-toluenesulfonic acid (7.3 g, 38.4 mmol) was added to the reaction mixture. The reaction mixture was heated at 80° C. for 16 hours and at 100° C. for 1.5 hours. It was cooled to room temperature and quenched with 2N sodium hydroxide solution and extracted with ethyl acetate. Organic layer was washed with water (3×150 ml) and brine. After drying over anhydrous magnesium sulfate, the solvent was evaporated and the residue was purified by flash chromatography on silica gel (30% acetone in hexane) to give the title B compound as a light yellow oil (4.0 g). $^1$H NMR (CDCl$_3$) δ 7.9 (s, 1H), 4.40 (q, J=6.4 Hz, 1H), 4.07 (m, 2H), 2.18 (s, 3H), 2.12 (t, J=7.6 Hz, 2H), 1.5 (pent, J=7.6 Hz, 2H), 1.4–1.2 (m, 5H), 1.02 (d, J=6.4 Hz, 3H), 0.82 (t, J=7.6 Hz, 3H); $^{13}$C NMR (CDCl$_3$) 167.2, 155.5, 148.3, 100.8, 59.3, 48.8, 36.4, 31.4, 22.5, 22.3, 19.2, 14.4, 13.8 ppm.

C. 2-Butyl-1-[2'-[(1,1-dimethylethoxy)-carbonyl][1,1'-biphenyl]-4-yl]-1,6-dihydro-4,6-dimethyl-5-pyrimidinecarboxylic Acid, Ethyl Ester The solution of the title B compound (1.0 g, 4.2 mmol) in dimethylformamide (14 mL) was treated with finely ground potassium carbonate (2.3 g, 16.8 mmol) and 4'-(bromomethyl)[1,1'-biphenyl]-2-carboxylic acid, 1,1-dimethylethyl ester (1.52 g, 5.0 mmol, prepared according to EP 253,310 to DuPont). The reaction mixture was allowed to stir at room temperature overnight. It was poured into water (100 ml) and extracted with ethyl acetate (2×150 ml). Organic layer was washed with water, brine and was dried over anhydrous magnesium sulfate. The solvent was evaporated to yield a yellow oil which was purified by flash chromatography on silica gel (5% methanol in chloroform) to provide the title C compound as a yellow foam (1.4 g). $^1$H NMR (CDCl$_3$) δ 7.76 (d, J=7.6 Hz, 1H), 7.46–7.24 (m, 7H), 4.80 (d, J=16.8 Hz, 1H), 4.47 (d, J=16.4 Hz, 1H), 4.33 (q, J=6.4 Hz, 1H), 4.10 (m, 2H), 2.4 (m, 2H), 2.35 (s, 3H), 1.60 (m, 2H), 1.5–1.1 (m, 17H), 0.90 (t, J=7.7 Hz, 3H); $^{13}$C NMR (CDCl$_3$) 167.7, 165.2, 163.9, 155.0, 141.8, 135.1, 132.6, 129.8, 129.7, 128.5, 128.2, 127.3, 126.2, 125.9, 101.9, 81.2, 77.2, 60.2, 54.1, 52.3, 34.0, 29.1, 27.6, 22.5, 18.4, 14.2, 13.7 ppm.

D. 2-Butyl-1-[[2'-carboxy[1,1'-biphenyl]-4-yl]methyl]-1,6-dihydro-4,6-dimethyl-5-pyrimidinecarboxylic Acid, Ethyl Ester, Trifluoroacetate To the solution of the title C compound (1.0 g, 2.2 mmol) in dichloromethane (10 mL) was added trifluoroacetic acid (3.0 mL) and the reaction mixture was stirred at room temperature for 3 hours. The solvent was evaporated and the residue was triturated with ethyl ether to provide the title compound (700 mg), m.p. 144°–146° C. $^1$H NMR (CDCl$_3$) δ 7.97 (d, J=7.7 Hz, 1H), 7.59 (t, J=7.7 Hz, 1H), 7.5–7.2 (m, 6H), 4.92 (d, J=16.8 Hz, 1H), 4.67 (d, J=15.8 Hz, 1H), 4.57 (q, J=5.9 Hz, 1H), 4.25 (q, J=7.1 Hz, 2H), 2.9 (m, 2H), 2.5 (s, 3H), 1.7 (m, 2H), 1.48 (q, J=7.1 Hz, 2H), 1.25 (m, 6H), 0.96 (t, J=7.0 Hz, 3H); $^{13}$C NMR (CDCl$_3$) 170.3, 164.8, 164.0, 144.3, 142.7, 141.4, 131.5, 130.9, 130.7, 130.6, 130.4, 129.8, 127.7, 126.5, 105.8, 61.2, 53.2, 52.9, 30.2, 29.1, 22.3, 18.9, 16.9, 14.1, 13.4 ppm.

Analysis calc'd for $C_{29}H_{33}F_3N_2O_6$: C, 61.91; H, 5.91; N, 4.99; F, 10.13; Found: C, 61.81; H, 5.99; N, 4.89; F, 10.43.

EXAMPLE 6

2-Butyl-1-[(2'-carboxy[1,1'-biphenyl]-4-yl)-methyl]-6-chloro-1,4-dihydro-4,4-dimethyl-5-pyrimidinecarboxylic Acid, Ethyl Ester, Monosodium Salt

A. 2-Butyl-6,6-dimethyl-4-oxo-1,4,5,6-tetrahydropyrimidine-5-carboxylic Acid, Ethyl Ester To the solution of the title A compound of Example 1 (3.53 g, 25.87 mmol) in dimethylformamide (7.0 mL) at 0° C. under argon was added potassium ter-butoxide (2.57 g, 22.85 mmol). The cooling bath was removed and the resulting suspension was stirred at room temperature for 30 minutes. To the reaction mixture was added diethyl isopropylidenemalonate (4.0 g, 19.9 mmol) in dimethylformamide (5 mL). It was stirred at room temperature overnight and then heated at 70° C. for 2 hours. The reaction mixture was diluted with water and extracted with ethyl acetate. The combined organic extracts were washed with water, brine and dried over anhydrous magnesium sulfate. The solvent was evaporated to give the title A compound as a light yellow oil (4.97 g). $^1$H NMR (CDCl$_3$) δ 9.6 (br s, 1H), 4.2 (m, 2H), 3.25 (s, 1H), 2.3 (t, J=7.7 Hz, 2H), 1.6 (qn, J=7.7 Hz, 2H), 1.38 (m, 2H), 1.32 (t, J=7.1 Hz, 3H), 1.26 (s, 6H), 0.91 (t, J=7.1 Hz, 3H); $^{13}$C NMR (CDCl$_3$) 168.2, 167.3, 152.3, 61.13, 56.18, 55.95, 34.95, 28.27, 27.8, 25.05, 21.9, 13.85, 13.5 ppm.

B. 6-Butyl-4-chloro-1,2-dihydro-2,2-dimethyl-5-pyrimidinecarboxylic Acid, Ethyl Ester The reaction mixture containing the title A compound (3.0 g, 11.9 mmol) in phosphorus oxychloride (10 mL) was heated at 120° C. for 5 hours. This layer chromatography of the reaction mixture indicated the presence of some starting material. Heating was continued for 5 more hours. The reaction mixture was cooled to room temperature and most of the phosphorus oxychloride was distilled off under vacuum. The brown residue in ethyl acetate was washed with 10% sodium carbonate, brine and dried over magnesium sulfate. The solvent was evaporated and the residue was purified by flash chromatography (ethyl acetate:hexanes/1:2 containing 0.01% triethyl amine) to give the title B compound as a light yellow oil (1.03 g) which solidified on standing. $^1$H NMR (CDCl$_3$) δ 4.30 (q, J=7.6 Hz, 2H), 2.24 (t, J=7.6 Hz, 2H), 1.62 (m, 2H), 1.55 (s, 6H), 1.44 (m, 2H), 1.4 (t, J=7.0 Hz, 3H), 0.98 (t, J=7.6 Hz, 3H); $^{13}$C NMR (CDCl$_3$) 165.66, 161.95, 109.1, 60.6, 55.1, 35.65, 30.2, 29.2, 22.3, 14.05, 13.7 ppm.

C. 2-Butyl-1-[2'-[(1,1-dimethylethoxy)-carbonyl][1,1'-biphenyl]-4-yl]-6-chloro-1,4-dihydro-4,4-dimethyl-5-pyrimidinecarboxylic Acid, Ethyl Ester To a solution of the title B compound (400 mg, 1.47 mmol) in dimethylformamide (5 mL) were added cesium carbonate (1.43 g, 4.41 mmol) and 4'-(bromomethyl)[1,1'-biphenyl]-2-carboxylic acid, 1,1-dimethylethyl ester (662 mg, 1.9 mmol, prepared according to EP 253,310, issued to DuPont) at room temperature under argon. The reaction mixture was stirred for 5 hours at room temperature and diluted with ether. The solid was filtered off and the filtrate was washed with water, brine and dried over anhydrous magnesium sulfate. The solvent was evaporated and the residue was purified by flash chromatography (20% ethyl acetate in hexanes) to yield the title C compound as a colorless oil (720 mg) which solidified on standing in the cold room. $^1$H NMR (CDCl$_3$) δ 7.86 (dd, J=1.2 and 7.7 Hz, 1H), 7.3–7.6 (m, 7H), 5.0 (s, 2H), 4.32 (q, J=7.0 Hz, 2H), 2.45 (t, J=7.0 Hz, 2H), 2.7 (m, 2H), 1.35–1.5 (m, 5H), 1.4 (s, 6H), 1.32 (s, 9H), 1.0 (t, J=7.0 Hz, 3H); $^{13}$C NMR (CDCl$_3$) 167.8, 165.9, 152.6, 141.4, 141.2, 136.3, 132.8, 130.6, 130.5, 130.4, 129.6, 129.0, 127.2, 126.3, 112.4, 81.2, 60.8, 55.4, 48.7, 34.0, 30.2, 29.5, 27.5, 22.32, 14.0, 13.8 ppm.

D. 2-Butyl-1-[(2'-carboxy[1,1'-biphenyl]-4-yl)methyl]-6-chloro-1,4-dihydro-4,4-dimethyl-5-pyrimidinecarboxylic Acid, Ethyl Ester, Monosodium Salt To the solution of the title C compound (785 mg, 1.46 mmol) in dichloromethane (5 mL) was added trifluoroacetic acid (4 mL) and the reaction mixture was stirred at room temperature overnight. The solvent was evaporated and the residue was coevaporated with toluene. The resulting oily product in methanol (2 mL) was converted to its sodium salt by treatment with 1N sodium hydroxide. Most of methanol was evaporated and the residue was passed through an HP-20 column eluting with 30% aqueous methanol. The product was lyophilized overnight to provide the title compound as a colorless solid (510 mg). $^1$H NMR (CD$_3$OD) δ 7.71 (d, J=8.2 Hz, 2H), 7.6 (m, 1H), 7.4 (m, 5H), 5.1 (s, 2H), 4.37 (q, J=7.0 Hz, 2H), 2.6 (m, 2H), 1.75 (m, 2H), 1.55 (m, 2H), 1.45 (t, J=7.0 Hz, 3H), 1.42 (s, 6H), 1.08 (t, J=7.0 Hz, 3H); $^{13}$C NMR (CD$_3$OD) 178.2, 167.1, 157.1, 142.9, 139.1, 137.2, 130.7, 130.2, 128.9, 128.2, 127.9, 127.6, 114.1, 62.2, 56.5, 34.5, 30.8, 30.3, 23.28, 14.4, 14.1 ppm.

Analysis calc'd for C$_{27}$H$_{30}$ClN$_2$O$_4$Na·0.75 H$_2$O: C, 62.55; H, 6.12; N, 5.40; Cl, 6.84; Found: C, 62.35; H, 6.03; N, 5.21; Cl, 7.15.

EXAMPLE 7

2-Butyl-1-[(2'-carboxy[1,1'-biphenyl]-4-yl]-methyl]-4-chloro-1,6-dihydro-6-phenyl-5-pyrimidinecarboxylic Acid, Ethyl Ester, Monosodium Salt

A. (trans)-2-Butyl-1,4,5,6-tetrahydro-4-oxo-6-phenyl-5-pyrimidinecarboxylic Acid, Ethyl Ester To the solution of the title A compound of Example 1 (1.98 g, 14.5 mmol) in dimethylformamide (6.0 mL) at 0° C. under argon was added potassium ter-butoxide (1.6 g, 14.0 mmol). The cooling bath was removed and the resulting suspension was stirred at room temperature for 30 minutes. To the reaction mixture was added diethyl benzalmalonate (3.0 g, 12.08 mmol) in dimethylformamide (5 mL). The reaction mixture was stirred at room temperature overnight. It was diluted with water and extracted with ethyl acetate. The combined organic extracts were washed with water, brine and dried over anhydrous magnesium sulfate. The solvent was evaporated and the residue was purified by flash chromatography to give the title A compound as a colorless oil (2.6 g). $^1$H NMR (CDCl$_3$) δ 9.4 (s, 1H), 7.4 (m, 5H), 5.14 (d, J=11.2 Hz, 1H), 4.22 (q, J=7.0 Hz, 2H), 3.56 (d, J=11.1 Hz, 1H), 2.4 (t, J=7.6 Hz, 2H), 1.7 (m, 2H), 1.5 (m, 2H), 1.23 (t, J=7.1 Hz, 3H), 1.0 (t, J=7.6 Hz, 3H); $^{13}$C NMR (CDCl$_3$) 167.9, 167.7, 154.6, 140.1, 128.7, 128.3, 127.8, 127.5, 126.9, 61.6, 61.2, 61.1, 53.7, 53.0, 28.2, 28.0, 22.1, 13.9, 13.7, 13.5 ppm.

B. 6-Butyl-4-chloro-1,2-dihydro-2-phenyl-3-pyrimidinecarboxylic Acid, Ethyl Ester The reaction mixture containing the title A compound (684 mg, 2.31 mmol) in phosphorus oxychloride (5 mL) was heated at reflux temperature (oil bath temperature 120° C.) for 6 hours under argon. Most of phosphorus oxychloride was distilled off under reduced pressure and the brown residue in ethyl acetate was washed with 10% sodium carbonate and brine. After drying over anhydrous magnesium sulfate, the solvent was evaporated to give the title B compound as a yellow oil (627 mg) which was used for the next reaction without purification.

C. 2-Butyl-1-[2'-[(1,1-dimethylethoxy)-carbonyl][1,1'-biphenyl]-4-yl]-4-chloro-1,6-dihydro-6-phenyl-5-pyrimidinecarboxylic Acid, Ethyl Ester The solution containing the title B compound (627 mg, 1.95 mmol) in dimethylformamide (5 mL) was treated with cesium carbonate (1.27 g, 3.9 mmol) and 4'-(bromomethyl) [1,1'-biphenyl]-2-carboxylic acid, 1,1-dimethylethyl ester (814 mg, 2.34 mmol, prepared according to EP 253,310 issued to DuPont). The reaction mixture was allowed to stir at room temperature overnight and diluted with ether. The solid was filtered off and the filtrate was washed with water, brine and dried over anhydrous magnesium sulfate. The solvent was evaporated and the residue was purified by flash chromatography to give the title C compound as a light yellow foam (624 mg). $^1$H NMR (CDCl$_3$) δ 7.85 (d, J=7.6 Hz, 1H), 7.3–7.6 (m, 12H), 5.4 (s, 1H), 4.78, 4.29 (ABq, J=16.4 Hz, 2H), 4.1 (m, 2H), 2.6 (m, 2H), 1.67 (m, 2H), 1.4 (m, 2H), 1.33 (s, 9H), 1.17 (t, J=7.1 Hz, 3H), 0.93 (t, J=7.7 Hz, 3H); $^{13}$C NMR (CDCl$_3$) 168.6, 165.1, 164.8, 143.1, 142.1, 133.9, 133.6, 131.7, 131.4, 130.7, 130.5, 129.8, 129.0, 128.5, 128.3, 127.1, 103.5, 82.2, 62.4, 61.3, 52.4, 35.0, 29.7, 28.6, 23.5, 14.9, 14.6 ppm.

D. 2-Butyl-1-[(2'-carboxy[1,1'-biphenyl]-4-yl]methyl]-4-chloro-1,6-dihydro-6-phenyl-5-pyrimidinecarboxylic Acid, Ethyl Ester, Monosodium Salt To the solution of the title C compound (600 mg, 1.02 mmol) in dichloromethane (5 mL) was added trifluoroacetic acid (4.0 mL) and the reaction mixture was stirred at room temperature overnight. The solvent was evaporated and the residue (605 mg) in methanol was converted to its sodium salt by treatment with 1N sodium hydroxide. Most of methanol was evaporated; the residue was passed through an HP-20 column (35% aqueous methanol) and lyophilized overnight to give the title compound as a colorless solid (340 mg). $^1$H NMR (CD$_3$OD) δ 7.71 (d, J=8.2 Hz, 2H), 7.6 (m, 1H), 7.45 (m, 10H), 5.5 (s, 1H), 5.0, 4.42 (ABq, J=16.4 Hz, 2H), 4.1 (m, 2H), 2.7 (m, 2H), 2.55 (m, 2H), 1.7 (m, 2H), 1.5 (m, 2H), 1.2 (t, J=7.0 Hz, 3H), 1.0 (t, J=7.0 Hz, 3H); $^{13}$C NMR (CD$_3$OD) 168.0, 166.5, 165.1, 162.0, 143.3, 142.6, 139.0, 134.5, 130.7, 130.1, 130.0, 128.9, 128.5, 128.2, 128.0, 127.7, 103.6, 62.5, 61.5, 530, 34.77, 30.2, 23.5, 14.4, 14.0 ppm.

Analysis calc'd for C$_{31}$H$_{30}$ClN$_2$O$_4$Na.1.4 H$_2$O: C, 64.35; H, 5.72; N, 4.84; Cl, 6.13; Found: C, 64.40; H, 5.55; N, 4.79; Cl, 5.98.

EXAMPLE 8

2-Butyl-1-[(2'-carboxy[1,1'-biphenyl]-4-yl)-methyl]-1,6-dihydro-6-methyl-4-phenyl-5-pyrimidinecarboxylic Acid, Ethyl Ester, Trifluoroacetate (1:1) Salt

A. Ethyl-2-(ethylidine) Benzoyl Acetate

To a mixture of ethyl benzoylacetate (21.3 g, 100 mmol) and acetaldehyde (4.8 g, 109 mmol) at −5° C. was added piperdine (0.3 g, 3.5 mmol) and the mixture was kept at this temperature for 48 hours. The reaction mixture was then neutralized with 10% sulfuric acid and diluted with ethyl ether. Organic layer was separated and washed with water (100 ml), dried over anhydrous magnesium sulfate and concentrated in vacuo to give the title A compound as an oil (21.0 g). $^1$H NMR (CDCl$_3$) δ 7.86 (d, J=7.1 Hz, 2H), 7.4 (m, 3H), 7.22 (d, J=7.7 Hz, 1H), 4.10 (q, J=7.6 Hz, 2H), 1.74 (d, J=7.1 Hz, 3H), 1.10 (t, J=7.1 Hz, 3H); $^{13}$C NMR (CDCl$_3$) 194.1, 165.1, 143.1, 133.4, 128.7, 128.5, 60.7, 15.1, 13.7 ppm.

B. 2-Butyl-1,6-dihydro-6-methyl-4-phenyl-5-pyrimidinecarboxylic Acid, Ethyl Ester To a solution of the title A compound of Example 1 (2.89 g, 21.1 mmol) in dimethylformamide (50 mL) was added potassium t-butoxide (2.2 g, 19.2 mmol) under argon and the reaction mixture was stirred for ~15 minutes. A solution of the title A compound (3.0 g, 19.2 mmol) in dimethylformamide 910 ml) was added and the reaction mixture was stirred for ~15 minutes and then p-toluenesulfonic acid (7.3 g, 38.4 mmol) was added to the reaction mixture at 0° C. The reaction mixture was heated at 80° C. for 16 hours and at 100° C. for 2 hours. The reaction mixture was then cooled and poured into 50% sodium hydroxide solution and extracted with ethyl acetate (3×200 ml). Organic layer was washed with water (3×150 ml) and brine. After drying over anhydrous magnesium sulfate, the solvent was evaporated and the residue was purified by flash chromatography on silica gel (10% hexane in ethyl acetate) to give the title B compound as a light yellow oil (3.5 g). $^1$H NMR (CDCl$_3$) δ 7.83 (m, 1H), 7.25 (m, 5H), 4.50 (q, J=6.5 Hz, 1H), 4.12 (m, 1H), 3.80 (m, 2H), 2.10 (m, 2H), 1.54 (m, 2H), 1.30 (m, 2H), 1.16 (d, J=6.4 Hz, 3H), 0.85 (t, J=4.7 Hz, 3H); $^{13}$C NMR (CDCl$_3$) 167.2, 155.5, 148.3, 100.8, 59.3, 48.8, 36.4, 31.4, 22.5, 22.3, 19.2, 14.4, 13.8 ppm.

C. 2-Butyl-1-[2'-[(1,1-dimethylethoxy)carbonyl]-[1,1'-biphenyl]-4-yl]-1,6-dihydro-6-methyl-4-phenyl-5-pyrimidinecarboxylic Acid, Ethyl Ester To a solution of the title B compound (1.0 g, 4.2 mmol) in dimethylformamide (14 mL) was treated with finely ground potassium carbonate (2.3 g, 16.8 mmol) and 4'-(bromomethyl)[1,1'-biphenyl]-2-carboxylic acid, 1,1-dimethylethyl ester (1.52 g, 5.0 mmol, prepared according to EP 253,310 issued to DuPont). The reaction mixture was allowed to stir at room temperature overnight. It was poured into water (100 ml) and extracted with ethyl acetate (2×150 ml). Organic layer was washed with water, brine and was dried over anhydrous magnesium sulfate. The solvent was evaporated to yield a yellow oil which was purified by flash chromatography on silica gel (5% methanol in chloroform) to provide the title C compound as a yellow foam (1.4 g). $^1$H NMR (CDCl$_3$) δ 7.76 (d, J=7.6 Hz, 1H), 7.46–7.24 (m, 7H), 4.80 (d, J=16.8 Hz, 1H), 4.47 (d, J=16.4 Hz, 1H), 4.33 (q, J=6.4 Hz, 1H), 4.10 (m, 2H), 2.4 (m, 2H), 2.35 (s, 3H), 1.60 (m, 2H), 1.5–1.1 (m, 17H), 0.90 (t, J=7.7 Hz, 3H); $^{13}$C NMR (CDCl$_3$) 167.7, 165.2, 163.9, 155.0, 141.8, 135.1, 132.6, 129.8, 129.7, 128.5, 128.2, 127.3, 126.2, 125.9, 101.9, 81.2, 77.2, 60.2, 54.1, 52.3, 34.0, 29.1, 27.6 22.5, 18.4, 14.2, 13.7 ppm.

D. 2-Butyl-1-[(2'-carboxy[1,1'-biphenyl]-4-yl)methyl]-1,6-dihydro-6-methyl-4-phenyl-5-pyrimidinecarboxylic Acid, Ethyl Ester, Trifluoroacetate (1:1) Salt To the solution of the title C compound (1.2 g, 2.1 mmol) in dichloromethane (15 mL) was added trifluoroacetic acid (5.0 mL) and the reaction mixture was stirred at room temperature for 3 hours. The solvent was evaporated and the residue was triturated with ethyl ether to provide the title compound (750 mg), m.p. 153°–155° C. $^1$H NMR (CDCl$_3$) δ 7.91 (d, J=6.4 Hz, 1H), 7.5 (t, J=5.9 Hz, 1H), 7.5–7.2 (m, 11H), 4.84 (d, J=5.2 Hz, 1H), 4.60 (d, J=19.3 Hz, 1H), 4.55 (m, 1H), 3.90 (m, 2H), 3.0 (m, 2H), 1.7 (m, 2H), 1.43 (t, J=7.0 Hz, 2H), 1.35 (d, J=6.4 Hz, 3H), 0.92 (t, J=7.1 Hz, 3H), 0.82 (t, J=7.1 Hz, 3H); $^{13}$C NMR (CDCl$_3$) 170.5, 165.5, 164.3, 145.1, 143.1, 141.7, 131.7, 131.0, 130.7, 130.2, 129.3, 128.2, 127.9, 127.1, 105.9, 61.4, 53.6, 53.4, 30.7, 29.5, 22.7, 19.2, 13.8, 13.6 ppm.

Analysis calc'd for C$_{34}$H$_{35}$F$_3$N$_2$O$_6$: C, 65.38; H, 5.65; N, 4.48; F, 9.12; Found: C, 65.23; H, 5.59; N, 4.47; F, 9.15.

EXAMPLE 9

2-Butyl-1-[(2'-carboxy[1,1'-biphenyl]-4-yl)-methyl]-1,6-dihydro-6-oxo-4-phenyl-5-pyrimidinecarboxylic Acid, Ethyl Ester, Monosodium Salt

A. 2-Butyl-1,6-dihydro-6-oxo-4-phenyl-5-pyrimidinecarboxylic Acid, Ethyl Ester To a solution of the title A compound of Example 7 (440 mg, 1.48 mmol) in benzene (5 mL) was added manganese oxide (388 mg, 4.46 mmol) and the reaction was stirred at room temperature overnight. It was heated at 70° C. (oil bath temperature) for 8 hours. More manganese oxide (488 mg) was added and the heating was continued overnight. The reaction mixture was cooled to room temperature and diluted with dichloromethane-methanol (10:1). It was filtered twice through a pad of silica gel and celite. The filtrate was evaporated and the residue was crystallized from isopropyl ether to provide the title A compound as a colorless solid (120 mg). The mother liquor was concentrated and purified by preparative chromatography (ethyl acetate:hexanes/50:50) to give additional material (41 mg) for a total of 178 mg, m.p. 143°–145° C. $^1$H NMR (CDCl$_3$) δ 7.6 (d, J=7.0 Hz, 2H), 4.4 (m, 3H), 4.15 (q, J=7.0 Hz, 2H), 2.7 (t, J=7.7 Hz, 2H), 1.75 (m, 2H), 1.4 (m, 2H), 1.05 (t, J=7.2 Hz, 2H), 0.9 (t, J=7.0 Hz, 3H).

Analysis calc'd for C$_{17}$H$_{20}$N$_2$O$_3$: C, 67.98; H, 6.71; N, 9.33; Found: C, 67.61; H, 6.70; N, 9.28.

B.

2-Butyl-1-[2'-[(1,1-dimethylethoxy)carbonyl][1,1'-biphenyl]-4-yl]-1,6-dihydro-6-oxo-4-phenyl-pyrimidine-5-carboxylic Acid, Ethyl Ester The solution containing the title A compound (172 mg, 0.58 mmol) in dimethylformamide (3 mL) was treated with cesium carbonate (378 mg, 1.16 mmol) and 4'-(bromomethyl)[1,1'-biphenyl]-2-carboxylic acid, 1,1-dimethylethyl ester (244 mg, 0.70 mmol, prepared according to EP 253,310 issued to DuPont). The reaction mixture was allowed to stir at room temperature for 2 hours and diluted with ethyl acetate. The solid was filtered off and the filtrate was washed with water, brine and dried over anhydrous magnesium sulfate. The solvent was evaporated and the residue was purified by flash chromatography (25% ethyl acetate in hexanes) to yield the title B compound (175 mg) as a colorless oil. $^1$H NMR (CDCl$_3$) δ 7.9 (m, 1H), 7.8 (m, 2H), 7.3–7.6 (m, 2 10H), 5.5 (s, 2H), 4.35 (q, J=7.0 Hz, 2H), 2.9 (t, J=7.7 Hz, 2H), 1.85 (m, 2H), 1.5 (m, 2H), 1.35 (s, 9H), 1.25 (t, J=7.6 Hz, 3H), 1.0 (t, J=7.0 Hz, 3H); $^{13}$C NMR (CDCl$_3$) 167.65, 165.9, 162.3, 160.3, 158.9, 141.6, 141.2, 136.9, 133.9, 132.7, 130.6, 130.4, 130.2, 129.6, 129.1, 128.3, 128.2, 127.2, 126.5, 116.3, 81.2, 61.6, 46.3, 34.8, 28.6, 27.5, 22.2, 13.7 ppm. The O-alkylated material, 2-butyl-4-[(2-carboxy[1,1-biphenyl]-4-yl)-6-phenyl-5-pyrimidinecarboxylic acid, 1,1-dimethylethyl ester, could also be isolated from the column.

C.

2-Butyl-1-[(2'-carboxyl[1,1-biphenyl]-4-yl)-methyl]-1,6-dihydro-6-oxo-4-phenyl-5-pyrimidinecarboxylic Acid, Ethyl Ester, Monosodium Salt To the solution of the title B compound (175 mg, 0.31 mmol) in dichloromethane (2 mL) was added trifluoroacetic acid (2.0 mL) and the reaction mixture was stirred at room temperature overnight. The solvent was evaporated and the residue in methanol was converted to its sodium salt by treatment with 1N sodium hydroxide. Most of the methanol was evaporated; the residue was passed through an HP-20 column eluting with 35% aqueous methanol. The product was lyophilized overnight to give the title C compound as a colorless solid (110 mg). $^1$H NMR (CD$_3$OD) δ 7.84 (m, 2H), 7.6–7.75 (m, 6H), 7.35–7.5 (m, 5H), 5.6 (s, 2H), 4.34 (q, J=7.6 Hz, 2H), 3.01 (t, J=7.6 Hz, 2H), 1.9 (m, 2H), 1.55 (m, 2H), 1.26 (t, J=7.1 Hz, 3H), 1.06 (t, J=7.0 Hz, 3H); $^{13}$C NMR (CDCl$_3$, free acid) 172.7, 165.6, 163.4, 160.5, 159.1, 142.6, 141.0, 136.0, 133.8, 132.1, 131.1, 130.7, 130.5, 129.1, 128.9, 128.3, 128.2, 128.1, 127.4, 126.6, 125.2, 116.4, 61.9, 46.9, 34.5, 28.9, 22.2, 21.4, 13.6 ppm.

Analysis calc'd for C$_{31}$H$_{29}$N$_2$O$_5$Na.1.5 H$_2$O: C, 66.57; H, 5.76; N, 5.01; Found: C, 66.67; H, 5.39; N, 4.91.

EXAMPLE 10

2-Butyl-1-[(2'-carboxy[1,1'-biphenyl]-4-yl)-methyl]-1,6-dihydro-4-methyl-6-oxo-5-pyrimidine-carboxylic Acid, Ethyl Ester, Monosodium Salt

A.

2-Butyl-1,6-dihydro-4-methyl-6-oxo-5-pyrimidinecarboxylic Acid, Ethyl Ester

To the solution of the title B compound of Example 1 (1.0 g, 4.16 mmol) in benzene (10 mL) was added manganese oxide (3.62 mg, 41.6 mmol) and the reaction was stirred at room temperature overnight. It was heated at 70° C. (oil bath temperature) for 24 hours. The reaction mixture was cooled to room temperature and diluted with dichloromethane-methanol (10:1). It was filtered (2x) through a pad containing silica gel and celite. The filtrate was evaporated to give a yellow oil (610 mg) which was purified by flash chromatography (EtOAc:hexanes/2:1) to provide the title A compound as a colorless solid (310 mg), containing a small amount of the unreacted starting material. $^1$H NMR (CDCl$_3$) δ 4.3 (q, J=7.0 Hz, 2H), 2.58 (t, J=7.6 Hz, 2H), 2.31 (s, 3H), 1.66 (m, 2H), 1.29 (t, J=7.0 Hz, 3H), 1.20 (m, 2H), 0.85 (t, J=7.0 Hz, 3H); $^{13}$C NMR (CDCl$_3$) 165.4, 162.8, 162.3, 162.0, 116.5, 61.3, 35.0, 29.4, 22.6, 22.0, 13.9, 13.4.

B.

2-Butyl-1-[2'-[(1,1-dimethyletoxy)-carbonyl][1,1'-biphenyl]-4-yl]-1,6-dihydro-4-methyl-6-oxo-pyrimidine-5-carboxylic Acid, Ethyl Ester To the solution containing the title A compound (300 mg, 1.26 mmol) in dimethylformamide (3 mL) were added cesium carbonate (815 mg, 2.5 mmol) and 4'-(bromomethyl) [1,1'-biphenyl]-2-carboxylic acid, 1,1-dimethylethyl ester (524 mg, 1.5 mmol, prepared according to EP 253,310 to DuPont). The reaction mixture was allowed to stir at room temperature for 4 hours and diluted with ethyl acetate. The solid was filtered off and the filtrate was washed with water, brine and dried over anhydrous magnesium sulfate. The solvent was evaporated and the residue was purified by flash chromatography (25% ethyl acetate in hexanes) to yield the title B compound (221 mg) as a colorless oil. $^1$H NMR (CDCl$_3$) δ 7.77 (dd, J=7.0 and 1.2 Hz, 1H), 7.3–7.5 (m, 2H), 7.25 (m, 5H), 5.34 (s, 2H), 4.4 (q, J=7.0 Hz, 2H), 2.7 (t, J=7.0 Hz, 2H), 2.4 (s, 3H), 1.7 (m, 2H), 1.4 (t, J=7.6 Hz, 3H), 1.23 (s, 9H), 0.9 (t, J=7.6 Hz, 3H); $^{13}$C NMR (CDCl$_3$) 167.6, 165.7, 162.4, 161.7, 159.6, 141.5, 141.1, 134.0, 132.7, 130.6, 130.3, 129.5, 129.0, 127.1, 126.3, 116.7, 81.1, 61.4, 46.2, 34.8, 28.9, 27.5, 22.4, 14.1, 13.6 ppm. The O-alkylated material, 2-butyl-4-[(2-carboxy[1,1-biphenyl]-4-yl)-6-methyl-5-pyrimidine carboxylic acid, 1,1-dimethylethyl ester, could also be isolated from the column.

C.

2-Butyl-1-[(2'-carboxyl[1,1-biphenyl]-4-yl)-methyl]-1,6-dihydro-4-methyl-6-oxo-5-pyrimidinecarboxylic Acid, Ethyl Ester, Monosodium Salt To the solution of the title B compound (220 mg, 0.44 mmol) in dichloromethane (4 mL) was added trifluoroacetic acid (3.0 mL) and the reaction mixture was stirred at room temperature overnight. The solvent was evaporated and the residue in methanol was converted to its sodium salt by treatment with 1N sodium hydroxide. Most of the methanol was evaporated; the residue was passed through an HP-20 column eluting with 30% aqueous methanol. The product was lyophilized overnight to give the title C compound as a colorless solid (166 mg). $^1$H NMR (CD$_3$OD) δ 7.64 (d, J=8.2 Hz, 2H), 7.55 (m, 1H), 7.4 (m, 3 H H), 7.29 (d, J=8.2 Hz, 2H), 5.5 (s, 2H), 4.45 (q, J=7.6 Hz, 2H), 2.85 (t, J=7.6 Hz, 2H), 2.45 (s, 3H), 1.75 (m, 2H), 1.5 (m, 5H), 1.0 (t, J=7.0 Hz, 3H); $^{13}$C NMR (CDCl$_3$, free acid) 172.1, 165.2, 164.1, 158.9, 158.4, 142.2, 141.2, 132.9, 132.0, 130.7, 129.4, 128.9, 128.1, 127.5, 126.4, 125.2, 116.9, 62.1, 47.2, 33.6, 29.6, 22.3, 20.1, 13.9, 13.3 ppm.

Analysis calc'd for C$_{26}$H$_{27}$N$_2$O$_5$Na.0.6 H$_2$O: C, 64,88; H, 5.90; N, 5.82; Found: C, 64.71; H, 5.79; N, 5.64.

EXAMPLE 11

2-Butyl-1-[(2'-carboxy[1,1'-biphenyl]-4-yl)-methyl]-4-[(4-chlorophenyl)]-1,6-dihydro-6-methyl-5-pyrimidinecarboxylic Acid, Ethyl Ester Trifluoroacetate (1:1) Salt

A. Ethyl-2-(ethylidine)-4-chlorobenzoyl Acetate

To a mixture of ethyl p-chlorobenzoyl-acetate (2.0 g, 8.8 mmol) and acetaldehyde (0.43 g, 9.7 mmol) at −5° C. was added piperdine (2 drops) and the mixture was kept at this temperature for 48 hours. The reaction mixture was then neutralized with 10% sulfuric acid and diluted with ethyl ether. Organic layer was separated and washed with water (100 ml), dried over anhydrous magnesium sulfate and concentrated in vacuo to give the title A compound (2.0 g) as an oil. $^1$H NMR (CDCl$_3$) δ 7.95 (d, J=8.7 Hz, 1H), 7.91 (d, J=8.3 Hz, 1H), 7.49 (m, 3H), 4.40 (q, J=7.0 Hz, 2H), 1.86 (d, J=7.0 Hz, 3H), 1.19 (t, J=7.1 Hz, 3H). $^{13}$C NMR (CDCl$_3$) 193.4, 164.1, 143.9, 130.6, 130.3, 128.7, 128.5, 60.9, 26.4, 15.7, 13.8 ppm.

B. 2-Butyl-4-chlorophenyl-1,6-dihydro-6-methyl-5-pyrimidinecarboxylic Acid, Ethyl Ester To a solution of the title A compound of Example 1 (1.29 g, 8.7 mmol) in dimethylformamide (30 mL) at 0° C. under argon was added potassium t-butoxide (0.9 g, 7.9 mmol) and the reaction mixture was stirred for ~15 minutes. A solution of the title A compound (2.0 g, 7.9 mmol) in dimethylformamide (10 ml) was added and the reaction mixture was stirred for ~15 minutes at 0° C. and then p-toluenesulfonic acid (3.0 g, 15.8 mmol) was added to the reaction mixture. The reaction mixture was heated at 80° C. for 16 hours and at 100° C. for 2 hours. It was cooled to room temperature and poured into 50% sodium hydroxide solution and extracted with ethyl acetate (3×200 ml). Organic layer was washed with water (3×150 ml) and brine. After drying over anhydrous magnesium sulfate, the solvent was evaporated and the residue was purified by flash chromatography on silica gel (30% hexane in ethyl acetate) to give a light yellow oil (1.0 g). $^1$H NMR (CDCl$_3$) δ 7.30 (d, J=7.7 Hz, 2H), 7.22 (d, J=8.2 Hz, 2H), 4.50 (q, J=6.4 Hz, 1H), 4.07 (q, J=7.0 Hz, 1H), 3.90 (q, J=5.9 Hz, 2H), 2.15 (m, 2H), 1.56 (m, 2H), 1.37 (q, J=7.0 Hz, 2H), 1.21 (d, J=6.4 Hz, 3H), 0.94 (2t, J=7.0 Hz, 6H); $^{13}$C NMR (CDCl$_3$) 166.3, 134.2, 130.0, 129.5, 128.8, 128.5, 127.8, 102.9, 59.5, 47.9, 34.9, 29.02, 22.5, 22.1, 113.6 ppm.

C. 6-Butyl-1-[2'-[(1,1-dimethylethoxy)carbonyl]-[1,1'-biphenyl]-4-yl]-4-chlorophenyl-1,6-dihydro-6-methyl-3-pyrimidinecarboxylic Acid, Ethyl Ester To solution of the title B compound (0.5 g, 1.5 mmol) in dimethylformamide (5 mL) was treated with cesium carbonate (0.97 g, 3.0 mmol) and 4-(bromomethyl)[1,1'-biphenyl]-2-carboxylic acid, 1,1-dimethylethyl ester (0.54 g, 1.8 mmol, prepared according to EP 253,310 issued to DuPont). The reaction mixture was allowed to stir at room temperature overnight. It was poured into water (100 ml) and extracted with ethyl acetate (2×150 ml). Organic layer was washed with water, brine and was dried over anhydrous magnesium sulfate. The solvent was evaporated to yield a yellow oil which was purified by flash chromatography on silica gel (20% ethyl acetate in hexane) to provide the title C compound (0.45 g) as a yellow foam. $^1$H NMR (CDCl$_3$) δ 7.70 (d, J=7.6 Hz, 1H), 7.36–7.22 (m, 11H), 4.76 (d, J=16.4 Hz, 1H), 4.47 (d, J=16.4 Hz, 1H), 4.35 (q, J=6.5 Hz, 1H), 3.83 (m, 2H), 2.4 (m, 2H), 1.60 (m, 2H), 1.30 (m, 2H), 1.18 (s, 9H), 0.82 (m, 6H); $^{13}$C NMR (CDCl$_3$) 167.6, 166.0, 162.5, 155.0, 141.5, 141.1, 139.0, 134.8, 133.7, 132.6, 130.5, 130.3, 130.0, 129.5, 129.1, 127.4, 127.1, 125.9, 103.3, 81.0, 59.5, 54.1, 52.5, 52.4, 34.1, 29.2, 27.4, 22.4, 18.3, 13.6, 13.5 ppm.

D. 2-Butyl-1-[(2'-carboxy[1,1'-biphenyl]-4-yl)methyl]-4-[(4-chlorophenyl)]-1,6-dihydro-6-methyl-5-pyrimidinecarboxylic Acid, Ethyl Ester Trifluoroacetate (1:1) Salt To the solution of the title C compound (0.45 g, 0.75 mmol) in dichloromethane (10 mL) was added trifluoroacetic acid (5.0 mL) and the reaction mixture was stirred at room temperature for 3 hours. The solvent was evaporated and the residue was triturated with ethyl ether to provide the title compound (370 mg), m.p. 131°–132° C. $^1$H NMR (CDCl$_3$) δ 7.91 (d, J=6.4 Hz, 1H), 7.53 (t, J=6.4 Hz, 1H), 7.5–7.2 (m, 10H), 4.88 (d, J=15.9 Hz, 1H), 4.60 (d, J=14.6 1H), 4.55 (m, 1H), 3.94 (m, 2H), 3.0 (m, 2H), 1.7 (m, 2H), 1.44 (t, J=7.7 Hz, 2H), 1.39 (d, J=8.2 Hz, 3H), 0.94 (t, J=7.0 Hz, 3H), 0.88 (t, J=7.6 Hz, 3H); $^{13}$C NMR (CDCl$_3$) 170.5, 165.3, 163.6, 143.7, 142.8, 141.3, 136.6, 131.4, 131.1, 130.6, 130.4, 129.9, 129.6, 128.2, 127.7, 126.9, 106.0, 61.2, 53.3, 53.1, 30.4, 29.2, 22.4, 18.9, 13.8, 13.4 ppm.

Analysis calc'd for C$_{34}$H$_{34}$F$_3$ClN$_2$O$_6$:

C, 61.95; H, 5.20; N, 4.25; Cl, 5.38; F, 8.65; Found: C, 61.99; H, 5.22; N, 4.25; Cl, 5.58; F, 8.64.

EXAMPLES 12–21

Using procedures outlined in Examples 1–5 and described in the literature discussed in this application, the following additional compounds can be prepared:

Example 12
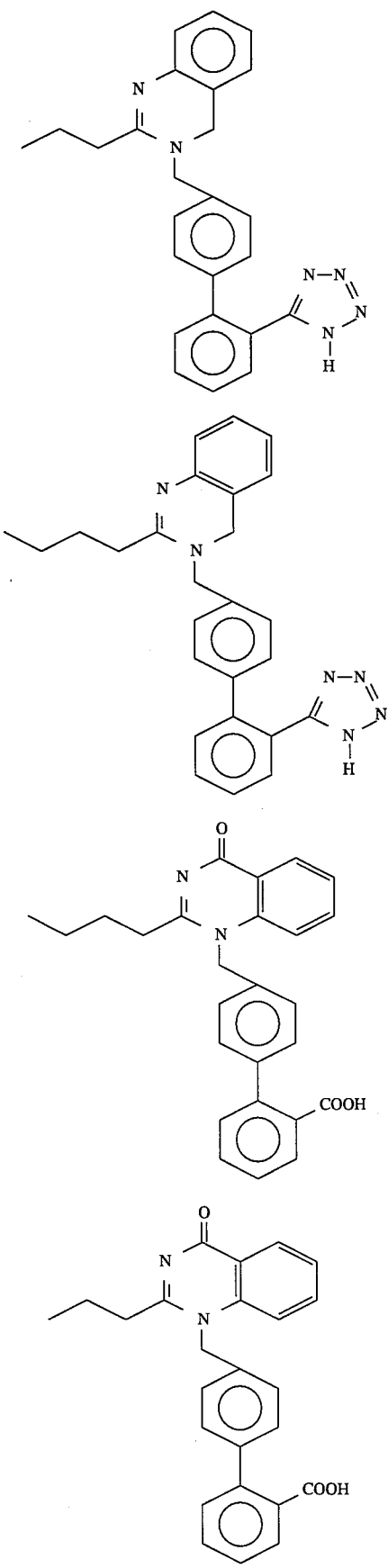
Example 13
Example 14
Example 15
-continued
Example 16
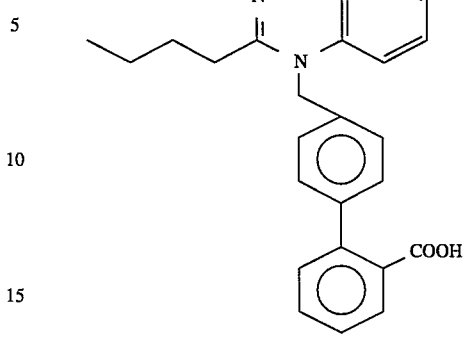
Example 17
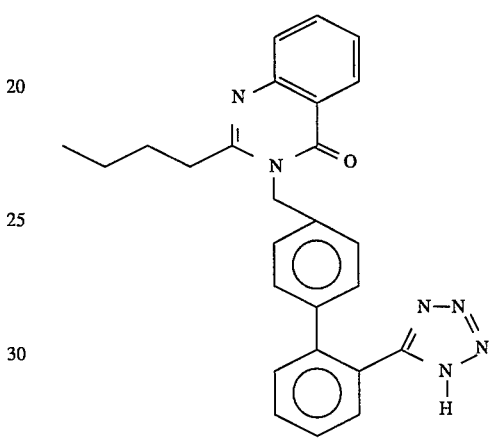
Example 18
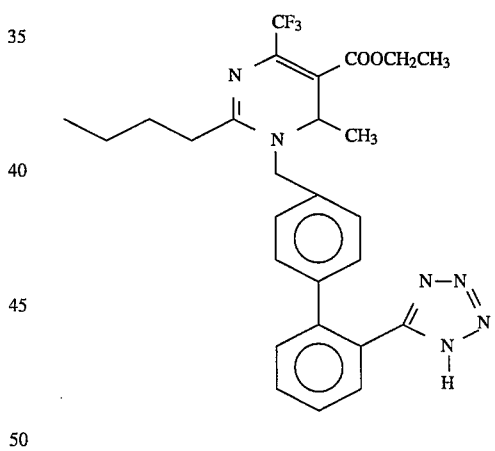

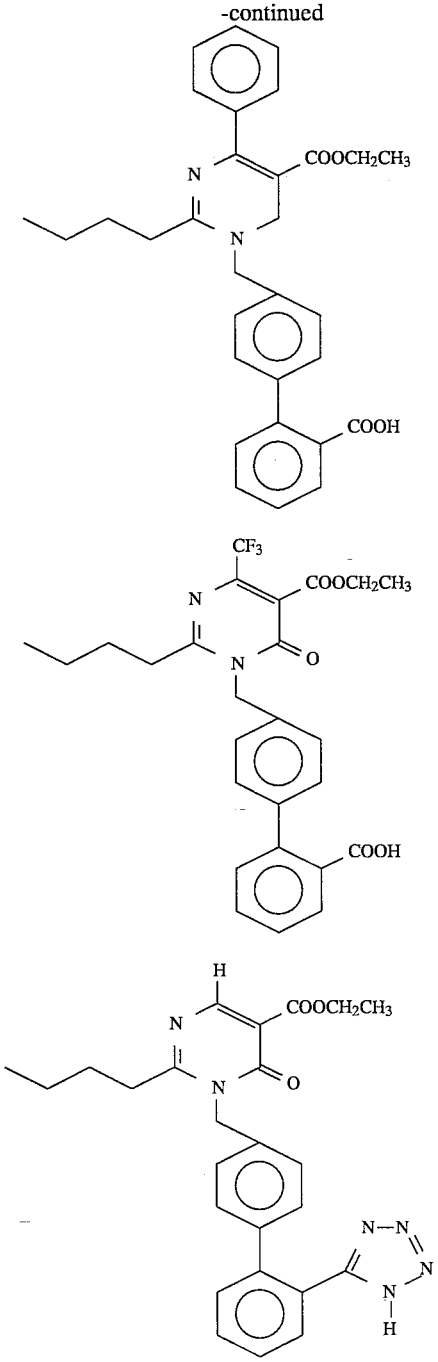

Example 19

Example 20

Example 21

What is claimed is:
1. A compound of the formula

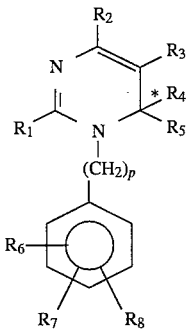

or its isomer

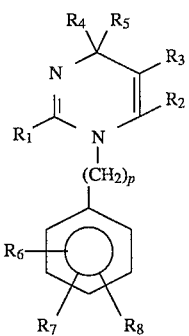

or pharmaceutically acceptable salts thereof
wherein $R_1$ is alkyl of 1 to 10 carbon atoms, alkenyl or alkynyl of 3 to 10 carbon atoms or the same groups substituted with F or —$CO_2R_{22}$; cycloalkyl of 3 to 8 carbon atoms, cycloalkylalkyl of 4 to 10 carbon atoms, cycloalkylalkenyl or cycloalkylalkynyl of 5 to 10 carbon atoms; —$(CH_2)_sZ(CH_2)_mR'$ (wherein R' is H, $C_{1-6}$alkyl, $C_{3-6}$cycloalkyl, $C_{2-4}$alkenyl or $C_{2-4}$alkynyl) optionally substituted with F or —$CO_2R_{22}$; benzyl or benzyl substituted on the phenyl ring with 1 or 2 halogens, alkoxy of 1 to 4 carbon atoms, alkyl of 1 to 4 carbon atoms, haloalkyl or nitro; —$SR_4$, —$OR_4$ (where $R_4 \neq H$) or —$NR_4R_5$;

$R_2$ is hydrogen, halogen, $R_4'$, —CN, haloalkyl, —$OR_4$, —$SR_4$ —$COOR_4$, $COR_4$, $(R_4'O)$alkyl, $(R_4'S)$alkyl, (substituted amino)alkyl;

$R_3$ is $R_4$, —COOR, —$CONH_2$, —CO-substituted amino, —COR, —CN, —$NO_2$,

—$SO_2R$ (wherein R is $R_4$, aminoalkyl or (substituted amino)alkyl), $(R_4'O)$alkyl, $(R_4'S)$alkyl, (substituted amino)alkyl, $(R_4'OOC)$alkyl, $(R_4'CO)$alkyl, (amino-CO)alkyl, (substituted amino-CO)alkyl, (ROCO)alkyl (wherein R is $R_4$ excluding hydrogen);

or $R_2$ and $R_3$ taken together are

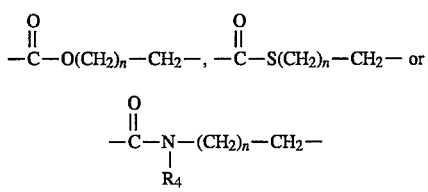

to form a 5- to 7-membered ring with the carbons to which they are attached;

or $R_2$ and $R_3$ taken together with the carbon atoms to which they are attached form an aryl;

$R_4'$ is selected from hydrogen, alkyl, alkenyl, alkynyl, aryl, arylalkyl, cycloalkyl, (cycloalkyl)alkyl, heterocyclo, (heterocyclo)alkyl, haloalkyl;

$R_4$ and $R_5$ are independently selected from alkyl, alkenyl, alkynyl, aryl, arylalkyl, cycloalkyl, (cycloalkyl)alkyl, heterocyclo, (heterocyclo)alkyl, haloalkyl;

$R_6$ is 4-$CO_2H$, 4-$CO_2R_9$,

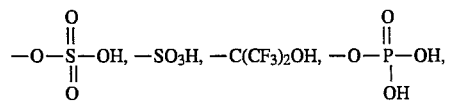

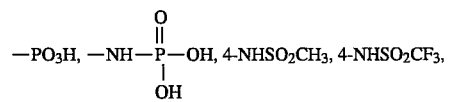

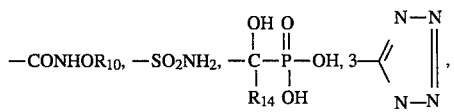

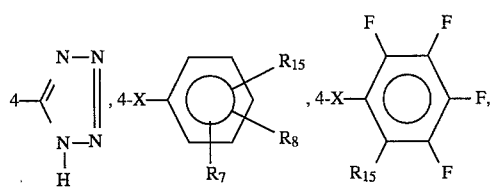

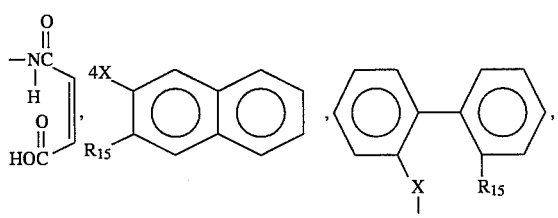

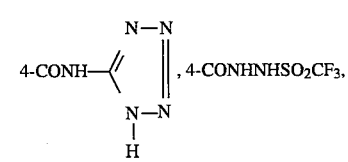

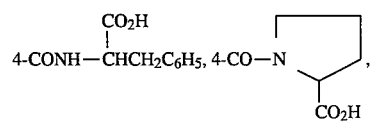

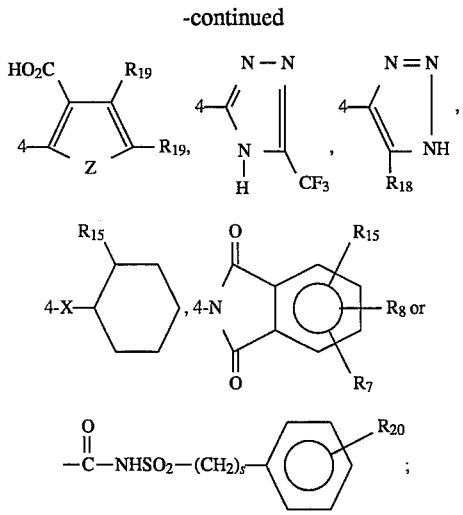

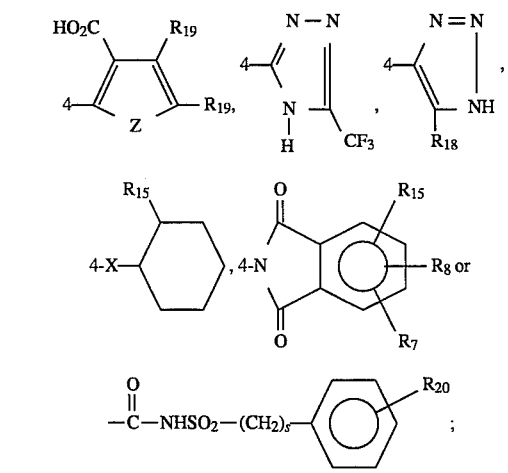

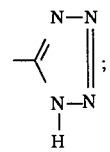

$R_7$ is hydrogen, halogen, —$NO_2$, —CN, alkyl of 1 to 4 carbons, acyloxy of 1 to 4 carbons, alkoxy of 1 to 4 carbons, —$CO_2H$, $CO_2R_9$, —$NHSO_2CH_3$, —$NHSO_2CF_3$, —$CONHOR_{10}$, —$SO_2NH_2$, aryl, furyl or

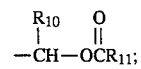

$R_8$ is hydrogen, halogen, alkyl of 1 to 4 carbons or alkoxy of 1 to 4 carbons;

$R_9$ is hydrogen or

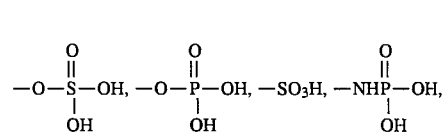

$R_{10}$ is hydrogen, methyl or benzyl;

$R_{11}$ is alkyl of 1 to 6 carbons, $NR_{12}R_{13}$;

$R_{12}$ and $R_{13}$ are independently hydrogen, benzyl, alkyl of 1 to 6 carbons or taken together are 3 to 6 methylene groups forming a 4- to 7-membered ring with the nitrogen atom to which they are attached;

$R_{14}$ is hydrogen, alkyl of 1 to 5 carbons or phenyl;

$R_{15}$ is —$CO_2H$, —$CO_2R_9$, —$CH_2CO_2H$, —$CH_2CO_2R_9$,

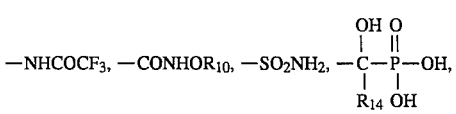

-continued

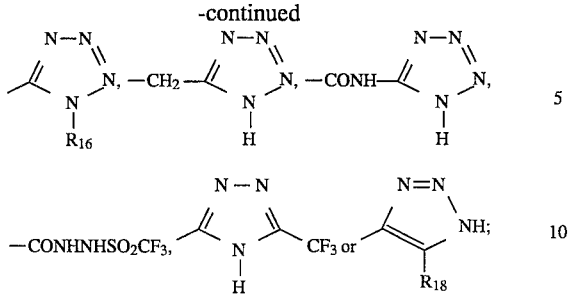

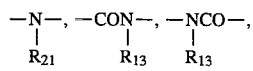

$R_{16}$ is hydrogen, alkyl of 1 to 4 carbons, —CH$_2$CH=CH$_2$ or —CH$_2$C$_6$H$_4$R$_{17}$;

$R_{17}$ is hydrogen, —NO$_2$, —NH$_2$, —OH or —OCH$_3$;

$R_{18}$ is —CN, —NO$_2$ or —CO$_2$R$_{19}$;

$R_{19}$ is hydrogen, alkyl of 1 to 6 carbons, cycloalkyl of 3 to 6 carbons, phenyl or benzyl;

$R_{20}$ and $R_{20}'$ are independently hydrogen, alkyl of 1 to 5 carbons or phenyl;

X is a carbon-carbon single bond, —CO—, —CH$_2$—, —O—, —S—, —N—, $$\begin{array}{ccc} -\text{N}-, & -\text{CON}-, & -\text{NCO}- \\ | & | & | \\ R_{21} & R_{13} & R_{13} \end{array}$$

—OCH$_2$—, —CH$_2$O—, —SCH$_2$—, —CH$_2$—S—, —NHC(R$_{20}$)(R$_{20}'$), —NR$_{13}$SO$_2$—, —SO$_2$NR$_{13}$—, —C(R$_{20}$)(R$_{20}'$)NH, —CH=CH—, —CF=CF—, —CH=CF—, —CF=CH—, —CH$_2$CH$_2$—, —CF$_2$CF$_2$—, $$\begin{array}{ccccc} \text{OR}_{22} & \text{OCOR}_{19} & \text{NR}_{23} & R_{24}\text{O} & \text{OR}_{25} \\ | & | & \| & \backslash \quad / & \\ -\text{CH}-, & -\text{CH}-, & -\text{C}- & \text{or} & -\text{C}- \quad ; \end{array}$$

$R_{21}$ is hydrogen, alkyl of 1 to 6 carbons, benzyl or alkyl;

$R_{22}$ is hydrogen, alkyl or perfluoroalkyl of 1 to 8 carbons, cycloalkyl of 3 to 6 carbons, phenyl or benzyl;

$R_{23}$ is —N(R$_{20}$)(R$_{20}'$), —NHCONH$_2$, —NHCSNH$_2$,

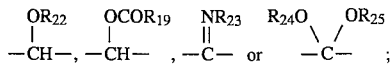

$R_{24}$ and $R_{25}$ are independently alkyl of 1 to 4 carbons or taken together are —(CH$_2$)$_q$;

Z is O, NR$_{19}$ or S;

m is 1 to 5;

n is 0 to 2;

p is 0 to 2;

q is 2 to 3; and s is 0 to 5;

wherein the term "alkyl", as used by itself or as part of a larger group, refers to groups having 1 to 10 carbon atoms;

the term "aryl" refers to phenyl, 1-naphthyl, 2-naphthyl, monosubstituted phenyl, 1-naphthyl, or 2-naphthyl wherein said substituent is alkyl of 1 to 4 carbons, alkylthio of 1 to 4 carbons, alkoxy of 1 to 4 carbons, halo, nitro, cyano, hydroxy, amino, —NH-alkyl wherein alkyl is of 1 to 4 carbons, —N(alkyl)$_2$, wherein alkyl is of 1 to 4 carbons, CF$_3$,

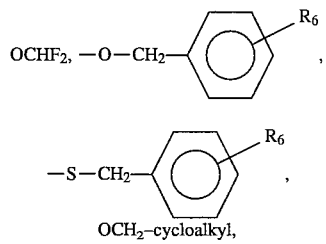

or —S—CH$_2$-cycloalkyl, and disubstituted phenyl, 1-naphthyl, or 2-naphthyl wherein said substituents are selected from methyl, methoxy, methylthio, halo, CF$_3$, nitro, amino, and OCHF$_2$;

the term "heterocyclo" refers to 2-thienyl, 3-thienyl, 2-furyl, 3-furyl, 2-pyridyl, 3-pyridyl, 4-pyridyl and imidazolyl wherein the pyridyls may be substituted with alkyl of 1 to 4 carbons, alkoxy of 1 to 4 carbons or alkylthio of 1 to 4 carbons; and the terms "substituted amino" refers to a group of the formula —NZ$_1$Z$_2$ wherein Z$_1$ is hydrogen, alkyl, or aryl-(CH$_2$)- and Z$_2$ is alkyl or aryl-(CH$_2$)$_m$- (where m is 0 to 2) or Z$_1$ and Z$_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl- 1-piperazinyl, 4-arylalkyl- 1-piperazinyl, 4-diarylalkyl-1-piperazinyl, or 1-pyrrolidinyl, 1-piperidinyl, or 1-azepinyl substituted with alkyl, alkoxy, alkylthio, halo, trifluoromethyl or hydroxy.

2. A compound of claim 1 wherein $R_1$ is alkyl of 3 to 5 carbons;

$R_2$ is hydrogen, alkyl, haloalkyl, chloro or aryl;

$R_3$ is —COOR;

$R_4$ is methyl;

$R_5$ is alkyl or aryl;

$R_6$ is —COOH or tetrazole;

$R_7$ is alkyl or hydrogen; and, $R_8$ is hydrogen.

3. A compound of claim 1 wherein $R_1$ is n-butyl;

$R_2$ is hydrogen, —CF$_3$, chloro, phenyl or 4-chlorophenyl;

$R_3$ is —COOC$_2$H$_5$;

$R_4$ is methyl;

$R_5$ is methyl or aryl;

$R_6$ is 2—COOH or 2-tetrazole;

$R_7$ is hydrogen; and, $R_8$ is hydrogen.

4. A compound of claim 1 having the name 2-butyl-1-[(2'-carboxy[1,1'-biphenyl]-4-yl)-methyl]-6-chloro-1,4-dihydro-4,4-dimethyl-5-pyrimidinecarboxylic acid, ethyl ester, monosodium salt.

* * * * *